(12) United States Patent
Owens et al.

(10) Patent No.: US 10,585,296 B2
(45) Date of Patent: Mar. 10, 2020

(54) HIGH SPEED SCANNING SYSTEM WITH ACCELERATION TRACKING

(71) Applicant: Apton Biosystems, Inc., Pleasanton, CA (US)

(72) Inventors: Windsor Owens, San Francisco, CA (US); Bryan Staker, Pleasanton, CA (US); Rob Hartlage, Sunnyvale, CA (US); Edvinas Zizminskas, Dublin, CA (US); David Stern, Mountain View, CA (US); Paul Heilman, San Carlos, CA (US)

(73) Assignee: APTON BIOSYSTEMS, INC., Pleasanton, CA (US)

( * ) Notice: Subject to any disclaimer, the term of this patent is extended or adjusted under 35 U.S.C. 154(b) by 0 days.

(21) Appl. No.: 15/910,778

(22) Filed: Mar. 2, 2018

(65) Prior Publication Data

US 2018/0252936 A1    Sep. 6, 2018

Related U.S. Application Data

(60) Provisional application No. 62/467,048, filed on Mar. 3, 2017.

(51) Int. Cl.
*H04N 5/232* (2006.01)
*G02B 27/64* (2006.01)
*G01D 5/347* (2006.01)
*G02B 26/10* (2006.01)

(52) U.S. Cl.
CPC ....... *G02B 27/644* (2013.01); *G01D 5/34746* (2013.01); *G02B 26/101* (2013.01); *H04N 5/232* (2013.01)

(58) Field of Classification Search
CPC combination set(s) only.
See application file for complete search history.

(56) References Cited

U.S. PATENT DOCUMENTS

| | | | |
|---|---|---|---|
| 2002/0018192 A1* | 2/2002 | Nishi | G03F 7/70358 355/53 |
| 2002/0196450 A1 | 12/2002 | Olszak et al. | |
| 2006/0072191 A1* | 4/2006 | Akiyama | G02B 21/0032 359/385 |
| 2006/0139660 A1 | 6/2006 | Kwan | |
| 2008/0029491 A1 | 2/2008 | Johnson et al. | |
| 2011/0249143 A1* | 10/2011 | Tatsumi | H04N 5/2355 348/229.1 |
| 2011/0304687 A1* | 12/2011 | Joshi | H04N 5/23238 348/36 |

(Continued)

OTHER PUBLICATIONS

PCT International Search Report and Written Opinion, PCT Application No. PCT/US2018/020737, dated May 30, 2018, 17 pages.

*Primary Examiner* — Md N Haque
(74) *Attorney, Agent, or Firm* — Wilson Sonsini Goodrich & Rosati

(57) ABSTRACT

Disclosed herein is a high throughput optical scanning device and methods of use. The optical scanning device and methods of use provided herein can allow high throughput scanning of a continuously moving object with a high resolution despite fluctuations in stage velocity. This can aid in high throughput scanning of a substrate, such as a biological chip comprising fluorophores. Also provided herein are improved optical relay systems and scanning optics.

8 Claims, 12 Drawing Sheets

(56) References Cited

U.S. PATENT DOCUMENTS

| 2014/0152793 | A1 | 6/2014 | Staker et al. |
| 2014/0152888 | A1 | 6/2014 | Staker et al. |
| 2014/0204196 | A1 | 7/2014 | Loney et al. |
| 2015/0022881 | A1* | 1/2015 | Loza Alvarez ........ G02B 21/06 359/385 |

* cited by examiner

HIGH SPEED SCANNING SYSTEM WITH ACCELERATION TRACKING

CROSS-REFERENCE TO RELATED APPLICATION

This application claims the benefit of U.S. Provisional Application No. 62/467,048, filed Mar. 2, 2017, the entire disclosure of which is hereby incorporated by reference in its entirety.

FIELD OF THE INVENTION

The invention relates to methods and instruments for generating a stable image of a continuously moving substrate in an optical system.

BACKGROUND OF THE INVENTION

Typical single-molecule, single-fluor sensitivity biological fluorescent optical scanning systems require low noise cameras with long exposure times. These systems often require a high precision and stable imaging platform situated on granite or equivalent. In addition, these systems employ "step and repeat" staging which necessitate high acceleration and deceleration as well as high mass in order to achieve high throughput, stable imaging of multiple fields. To scan a large area chip (2000 mm$^2$) in a short amount of time (~5 min) at high magnification requires frame imaging times shorter than step and repeat systems allow.

An "image on the fly" approach is needed to prevent a loss in throughput due to stage accelerations and settling time inherent to the step and repeat systems. Traditional image on the fly applications require sample stages that can provide near-constant (~+/−0.05%) velocity, and scanning optics that image the sample as it moves. If the stage velocity is not near-constant throughout its travel, then the scanning optics will not image the exact same region of the sample as the stage moves. This can result in a blurry image (e.g., with a pixel smear of ~+/−3 pixels). This problem is typically solved by utilizing expensive stages that provide near constant velocity by using heavy stages and powerful stage drives. Unfortunately, this adds to the cost of the product and makes it impractical to use as a benchtop system.

Typical low-cost, compact and/or lightweight stages are built with components that have various surface irregularities such as pits, burrs, machining grooves, divots and misshapen cavities. These irregularities usually result in velocity that is not constant. For instance, a burr or a divot in the ways of a stage will cause the stage to momentarily slow down and then possibly speed up before returning to the velocity it had before it encountered the irregularity. The velocity fluctuations of the stage make the use of these low-cost, smaller components incompatible with current image on the fly high throughput scanning approaches due to the generation of unacceptable levels of image blur.

What is needed therefore, are improved scanning optics that increase the velocity fluctuation tolerance, allowing an image with increased stability (e.g., reduced pixel smear) to be obtained using image on the fly scanning with single fluor sensitivity in smaller, lightweight, and low-cost optical scanning systems.

SUMMARY OF THE INVENTION

The instant invention is based, at least in part, on the discovery of new methods and devices to reduce pixel smear in the imaging of an object on a moving stage.

Accordingly, provided herein is an optical scanning system for imaging a moving substrate, comprising a stage, said stage capable of moving along an axis, said stage configured to hold a substrate comprising a plurality of fields; an objective lens; a camera capable of acquiring an image of one of said plurality of fields through the objective lens, said image acquired via an optical path defined from one of said plurality of fields through said objective lens to said camera during acquisition of said image; a velocity tracking mirror mounted along said optical path; a first electrical motor operably coupled to said velocity tracking mirror to adjust the angle of the tracking mirror along said axis of stage movement in said optical path; a controller module operably coupled to said first electrical motor to send a first driving signal to said first electrical motor, wherein said first driving signal is a function of a velocity measurement of the stage movement along said axis; an acceleration tracking mirror mounted along said optical path; a second electrical motor operably coupled to said acceleration tracking mirror to adjust the angle of the acceleration tracking mirror along said axis of stage movement in said optical path, wherein said controller module is operably coupled to said second electrical motor to send a second driving signal to said second electrical motor, wherein said second driving signal is a function of the change of the stage velocity along said axis.

In some embodiments, the first or second driving signal is an electrical signal. In some embodiments, the first driving signal comprises a non-sinusoidal waveform. In some embodiments, the non-sinusoidal waveform is a sawtooth wave. In some embodiments, the first electrical motor is a galvanometer. In some embodiments, the second electrical motor is a piezoelectric actuator. In some embodiments, the first electrical motor or said second electrical motor are dual axes motors.

In some embodiments, the system further comprises a linear displacement sensor operably coupled to said controller module to send a signal comprising a positional measurement of said substrate or said stage to said controller module. In some embodiments, the linear displacement sensor is a linear encoder.

In some embodiments, the first driving signal is a function of a velocity determined from said positional measurement. In some embodiments, the second driving signal is a function of a change in velocity determined from said positional measurement.

In some embodiments, the first or second signal comprises a waveform that is a function of the field scan frequency. In some embodiments, the first or second signal comprises a waveform that is a function of the imaging duty cycle.

In some embodiments, the movement of said velocity tracking mirror and said acceleration tracking mirror reduce a tracking error of said field by said camera as compared to without movement of said acceleration tracking mirror. In some embodiments, the tracking error is reduced to less than 0.1%. In some embodiments, the tracking error is reduced to less than 1 pixel.

In some embodiments, the velocity tracking mirror and the acceleration tracking mirror are adjacent components along said light path.

In some embodiments, the system comprises a plurality of cameras. In some embodiments, the system further comprises a beam splitter mounted along said light path, wherein said beam splitter is mounted along said light path after said velocity tracking mirror and acceleration tracking mirror and before said plurality of cameras.

In some embodiments, the system further comprises an illumination path, said illumination path extending from an illumination element to one of said plurality of fields.

In some embodiments, the illumination element comprises an excitation laser operably mounted to transmit an excitation light to said field, wherein said optical path comprises fluorescent light emitted from said field to said camera. In some embodiments, the excitation light is not transmitted to said camera. In some embodiments, the illumination element comprises an illumination light operably mounted to transmit an illumination light to said field. In some embodiments, the illumination light is mounted underneath the field such that the optical path comprises light transmitted through said field and to said camera. In some embodiments, the illumination light is mounted above or transverse to said field such that the optical path comprises light reflected by said field and to said camera.

In some embodiments, the system further comprises a third electrical motor operably mounted to the objective lens to move the objective lens along said optical path, thereby maintaining said field in focus. In some embodiments, the third electrical motor is operably connected to said controller module to receive a third driving signal that is a function of the movement of the field out of the focal plane, such that the objective lens is moved to maintain said field in focus by said camera.

In some embodiments, the system further comprises at least one additional pair of mirrors comprising a second velocity tracking mirror and a second acceleration tracking mirror, wherein said mirrors are operably mounted to said device to reduce a tracking error of said field by said camera along a different axis.

Also provided herein is a method of imaging a plurality of fields on a moving substrate, comprising providing an optical scanning system comprising a moveable stage holding a substrate comprising a plurality of fields, a camera, an objective lens, a velocity tracking mirror, and an acceleration tracking mirror; moving said moveable stage along an axis, thereby moving said substrate comprising a plurality of fields along said axis; and concurrent with said movement, capturing an image of one of said plurality of fields passing through said objective lens using said camera, wherein said image of said field is stabilized during said image capture by rotating said velocity tracking mirror as a function of a velocity of the moveable stage along said axis, and rotating said acceleration tracking mirror as a function of a change in the velocity of the moveable stage along said axis.

In some embodiments, the method of imaging a plurality of fields on a moving substrate further comprises obtaining a measurement of the velocity of said moveable stage, said substrate, or said field along said axis, and adjusting said first driving signal as a function of said velocity. In some embodiments, the method of imaging a plurality of fields on a moving substrate further comprises determining a change in velocity of said moveable stage from a plurality of velocity measurements, and adjusting said second driving signal as a function of said change in velocity.

In some embodiments, the rotation of the velocity tracking mirror or the acceleration tracking mirror is performed based on said measured velocity or said measured change in velocity. In some embodiments, the first driving signal is a function of an anticipated velocity of said stage. In some embodiments, the second driving signal is a function of an anticipated change in velocity of said stage.

In some embodiments, the velocity tracking mirror is operably coupled to a first electric motor. In some embodiments, the first electric motor is a galvanometer. In some embodiments, the optical scanning system comprises a controller module, and wherein said first electric motor is operably coupled to said controller module.

In some embodiments, rotating said velocity tracking mirror comprises sending a first driving signal from said controller module to said first electric motor. In some embodiments, the first driving signal is a function of a measured or predetermined velocity of the substrate.

In some embodiments, the acceleration tracking mirror is operably coupled to a second electric motor. In some embodiments, the electric motor is a piezoelectric actuator. In some embodiments, the electric motor is operably coupled to said controller module. In some embodiments, the acceleration tracking mirror comprises sending a second driving signal from said controller module to said second electric motor.

In some embodiments, the second driving signal is a function of a measured or predetermined change in the velocity of the substrate. In some embodiments, the second driving signal is a function of a deviation of said velocity from the velocity used to determine said first driving signal.

In some embodiments, the velocity tracking mirror and the acceleration tracking mirror are adjacent.

In some embodiments, the movement of said velocity tracking mirror and said acceleration tracking mirror reduce a tracking error of said field by said camera as compared to without movement of said acceleration tracking mirror. In some embodiments, the tracking error is reduced to less than 0.1%. In some embodiments, the tracking error is reduced to less than 1 pixel.

In some embodiments, the method further comprises adjusting the location of the objective lens along the optical path to maintain said field in focus during said image capture. In some embodiments, the adjustment of the objective lens maintains an intensity jump between two adjacent pixels of said image of greater than 50%, 60%, 70%, 80%, or 90%.

In some embodiments, the optical scanning system further comprises a second velocity tracking mirror and a second acceleration tracking mirror, further comprising, concurrent with said movement of said moveable stage and said image capture of one of said plurality of fields: rotating said second velocity tracking mirror as a function of a velocity of the moveable stage along a second axis, and rotating said second acceleration tracking mirror as a function of a change in the velocity of the moveable stage along said second axis thereby stabilizing imaging of said field for at least two axes simultaneously.

In some embodiments, the method further comprises rotating each of a plurality of pairs of velocity tracking and acceleration tracking mirrors to stabilize an image for a corresponding plurality of distinct axes.

In some embodiments, the frequency of image capture is at least 20 Hz, 40 Hz, 60 Hz, 80 Hz, 100 Hz, 120 Hz, 140 Hz, 160 Hz, 180 Hz, or 200 Hz. In some embodiments, the duty cycle of the image capture is at least 1%, 2%, 3%, 4%, 5%, 6%, 7%, 8%, 9% or 10%. In some embodiments, the duty cycle of the image capture is at least 10%, 20%, 30%, 40%, 50%, 60%, 70%, 80% or 90%.

Also provided herein is a method of reducing positioning error in an image obtained from a moving stage, comprising: measuring a velocity of said moving stage; determining an error correction term from said measured velocity as a function of the difference between the measured velocity of said stage and an anticipated velocity of said stage; generating a driving signal as a function of said error correction term; and sending said driving signal to an electrical motor, wherein said electrical motor is operably connected to a tracking mirror to actuate rotation of said tracking mirror. In some embodiments, the motor is a galvanometer or a piezo-electric actuator.

Also provided herein is an optical scanning system for imaging a moving substrate, comprising: a stage, said stage capable of moving along an axis, said stage configured to hold a substrate comprising a plurality of fields; an objective lens; a camera capable of acquiring an image of one of said plurality of fields through the objective lens, said image acquired via an optical path defined from one of said plurality of fields through said objective lens to said camera during acquisition of said image; a motion tracking mirror mounted along said light path; an electric motor operably coupled to said motion tracking mirror to actuate angular motion of the tracking mirror along said axis of stage movement in said optical path; and a controller module operably coupled to said electric motor to send a driving signal to said electric motor, wherein said controller module is capable of generating said driving signal as a function of a velocity fluctuation of said stage or substrate movement along said axis.

In some embodiments, the device comprises a velocity sensor in electrical communication with the controller module, said velocity sensor capable of detecting positional or velocity information of the substrate or stage and sending said information to the controller module, wherein said controller module is configured to generate said driving signal as a function of the velocity signal received from the velocity sensor.

In some embodiments, the sensor is a linear encoder. In some embodiments, the linear encoder is a non-interferometric encoder. In some embodiments, the linear encoder is optical, magnetic, capacitive, inductive, or uses an Eddy current. In some embodiments, the sensor is calibrated for velocity feedback across the moveable stage.

In some embodiments, the driving signal is a function of both a pre-determined velocity and a measured velocity. In some embodiments, the stage comprises a mechanical bearing positioned to facilitate movement of said stage along an axis. In some embodiments, the objective lens has a magnification selected from the group consisting of: 5×, 10×, 20×, 30×, 40×, 50×, 60×, 70×, 80×, 90×, or 100×.

Also provided herein is a method of imaging a plurality of fields on a moving substrate, comprising: providing an optical scanning system comprising a moveable stage holding a substrate comprising a plurality of fields, an objective lens, a camera, a motion tracking mirror, and an electric motor operatively coupled to said motion tracking mirror to effect movement of said motion tracking mirror to track said movement of said moveable stage along said axis during an image capture, and to return said motion tracking mirror to an initial position after said image capture; moving said moveable stage along an axis, thereby moving said substrate comprising a plurality of fields along said axis; and generating an image for each of M fields of said substrate, performing at least M image capture cycles during movement of said moveable stage along said axis, each cycle comprising: providing a cycle M driving signal to an electric motor to control movement of said tracking mirror to track the velocity of said moveable stage along said axis; capturing an image of said field while said tracking mirror is tracking said moving stage; and determining an average velocity of said field, wherein said average velocity is used to generate a cycle M+1 driving signal to control movement of said electric motor during cycle M+1.

In some embodiments, the frequency of image capture is at least 20 Hz, 40 Hz, 60 Hz, 80 Hz, 100 Hz, 120 Hz, 140 Hz, 160 Hz, 180 Hz, or 200 Hz. In some embodiments, the duty cycle of the image capture is at least 1%, 2%, 3%, 4%, 5%, 6%, 7%, 8%, 9% or 10%. In some embodiments, the duty cycle of image capture is at least 10%, 20%, 30%, 40%, 50%, 60%, 70%, 80% or 90%.

In some embodiments, the method further comprises performing an initial cycle to determine an average velocity of said field, wherein no image capture occurs. In some embodiments, the M+1 driving signal comprises a correction term that is a function of the difference between a measured velocity and a desired velocity of said moveable stage along said axis. In some embodiments, determining said average velocity of said field comprises measuring one or more positions of a field at a time. In some embodiments, the average velocity of said field further comprises comparing said measured position of said field at said time with a previously measured position and time of another field.

In some embodiments, the velocity feedback loop duration from positional measurement of field M to providing said M+1 driving signal is no more than 100 ms and could be as low as 2 ms., 90 ms, 80 ms, 70 ms, 60 ms, 50 ms, 40 ms, or 30 ms. In some embodiments, the average velocity is determined by collecting information about the position of the substrate at a frequency of no more than 250 kHz, 200 kHz, 150 kHz, 100 kHz, 50 kHz, 20 kHz, 10 kHz, 5 kHz, 2 kHz, 1000 Hz, 500 Hz, 240 Hz, 120 Hz, 60 Hz, or 30 Hz.

In some embodiments, the generated image has a pixel smear of no more than +/−one pixel. In some embodiments, the pixel comprises a cross-sectional distance along said axis of about 150 nm on said substrate.

In some embodiments, the image is generated from a substrate moving at a velocity in a range from 100 μm/second to 1,000 mm/second. In some embodiments, the movement of said moveable stage along said axis comprises velocity fluctuations in the range of 0.1% to 1% of the average velocity.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 7A is related to a dual mirror embodiment, while FIG. 7B is related to a single mirror embodiment.

DETAILED DESCRIPTION

Figure 1:
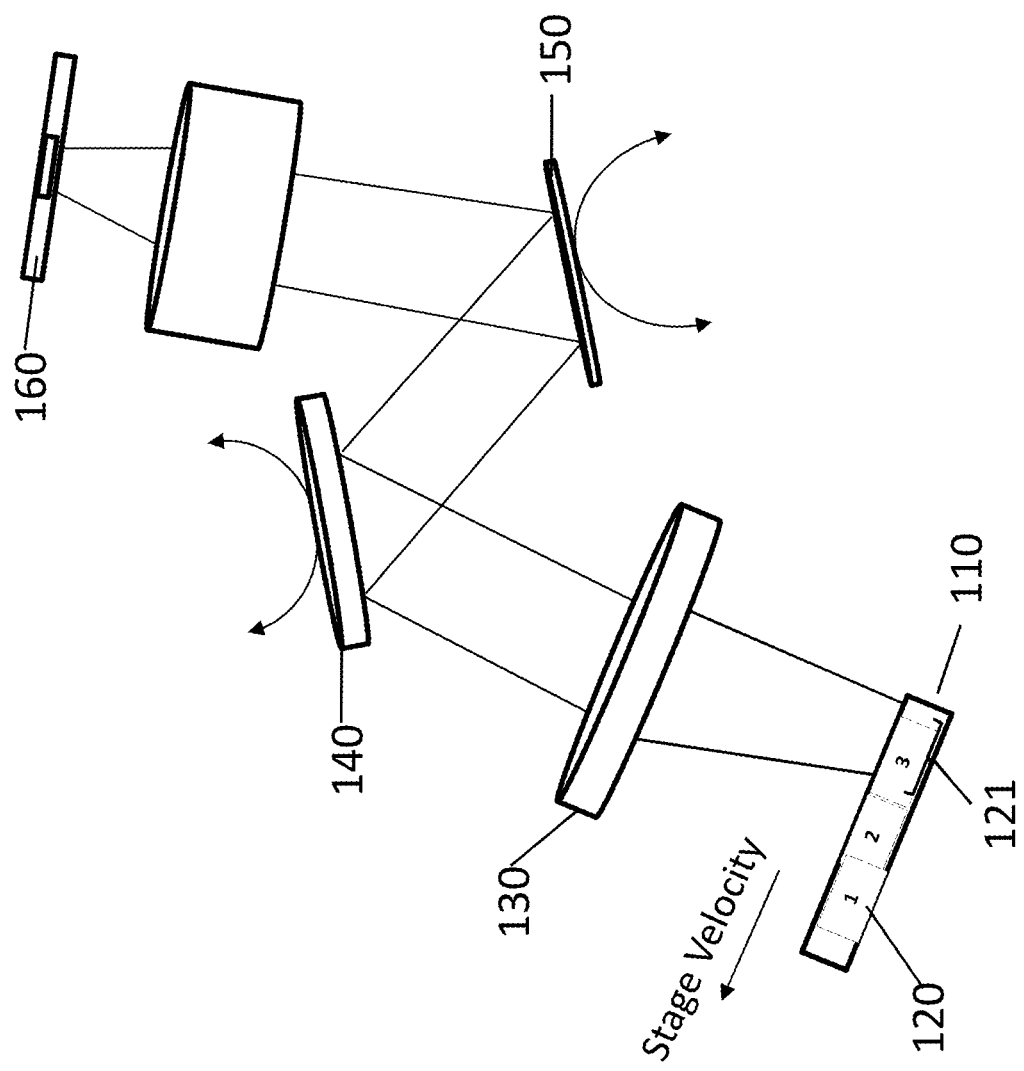
FIG. 1 is a diagram of components of an optical scanning device along an optical path from a substrate to a detector comprising an acceleration tracking mirror and a velocity tracking mirror (i.e., a dual mirror embodiment) according to an embodiment of the invention.

The details of various embodiments of the invention are set forth in the description below. Other features, objects, and advantages of the invention will be apparent from the description and the drawings, and from the claims.

As used herein, the term "objective lens" refers to an element or group of elements, in an optical scanning system, that comprises one or more lenses and is configured and operative to magnify an electromagnetic (e.g., such as optical) signal. In some embodiments, an objective lens has a large numerical aperture (NA), such as an NA in a range between 0.6 and 1.5 and performs imaging via air immersion or liquid immersion (e.g., such as water, oil, or other immersion fluids). In various embodiments, an objective lens may have a focal length in the range from 2 mm to 25 mm.

As used herein, the term "substrate" refers to an object having a multitude of distinct features that are targets for imaging. These features may or may not be arranged in a spatially uniform pattern. For example, in some embodiments a substrate comprises a non-planar structure with a surface, such as a bead or a well, to which target biomolecules have been attached as the target features. In another example, in some embodiments a substrate comprises an array chip. An array chip (i.e., an array, microarray, or chip) refers to a solid phase support having a surface, preferably but not exclusively a planar or substantially planar surface, that carries attachment sites to which target biomolecules (e.g., such as proteins or nucleic acids) have been attached as the target features.

As used herein, the term "field" refers to an area of a substrate capable of being captured within a single image by a camera. A field on the substrate is related to the field of view of the camera. An entire substrate may be scanned by taking images of a plurality of fields on a substrate.

As used herein, the term "optical path" or "light path" refers to the path of light or other electromagnetic radiation from a source to the camera sensor. Manipulation of the optical path by mirrors along the optical path enable the capture of a still image from a continuously moving substrate with random or systematic velocity fluctuations.

As used herein, the term "scanning" refers to operations to observe and record the status of a substrate.

As used herein, the term "velocity tracking mirror" refers to a mirror configured to track the movement of a substrate at a velocity. This velocity may be fixed or variable. The velocity may be predetermined, or may include systematic or random error in the velocity.

As used herein, the term "velocity tracking error" refers to an error in the tracking of a substrate or stage velocity by the velocity tracking mirror. In some embodiments, this is the result of a deviation in the velocity of the substrate from the velocity being tracked by the velocity tracking mirror.

As used herein, the term "acceleration tracking mirror" refers to a mirror that is operably connected to an optical scanning system to rotate in response to a nonlinearity, such as a systematic or random error in stage velocity, or any other deviations from an expected or constant stage velocity. In some embodiments, the acceleration tracking mirror is paired with a velocity tracking mirror to provide a still image of a moving substrate with reduced pixel smear.

As used herein, the term "electrical motor" refers to a device that converts an electrical signal to a physical movement, such as a motor that rotates in response to electrical energy. In some embodiments, the electrical motor provides a rotation mechanism for rotating a velocity tracking mirror or an acceleration tracking mirror. The electrical motor can be operably linked to a controller module that sends an electrical signal or driving signal to effect controlled movement of the electrical motor. An electrical motor may be a galvanometer or a piezoelectric actuator. As used herein, a "galvanometer" refers to a coil in a magnetic field that moves in response to an electrical signal. This can act as an electrical motor to actuate rotary motion of a tracking mirror. As used herein, the term "piezoelectric actuator" refers to a type of electric motor based upon the change in shape of a piezoelectric material when an electric field is applied. Although electrical motors are referred to in this specification as a preferred embodiment, other devices to provide actuation of components of the parts of the invention described herein, such as those based on hydraulics, pneumatics, or magnetic principles may also be used.

As used herein, the term "controller module" refers to one or more components in the device that provide control over components of the optical scanning system. In particular, the controller module includes devices that control movement of the electrical motors operably connected to one or more tracking mirrors. Thus, the controller module generates and transmits a driving signal to these electrical motors. The driving signal may be generated from a pre-programmed or observed stage or substrate motion. The driving signal may be generated from information collected by a position or velocity sensor, such as an encoder, and used to generate a velocity measurement that is then translated into a responsive driving signal to control movement of one or more tracking mirrors.

As used herein, the term "electrical signal" or "driving signal" refers to a controlled amount of energy sent to an electrical motor that the motor transforms into physical movement. For example, a galvanometer can effect rotation of a mirror to track a moveable stage and to return to its original position after imaging is complete by sending a drive signal that resembles a sawtooth wave.

As used herein, the term "duty cycle" refers to the percent of time a tracking mirror is tracking the stage and the camera is imaging the field (as opposed to flyback time, where the tracking mirror is returning to its initial position).

As used herein, the term "imaging frequency" or "image capture frequency" refers to the frequency of image capture of fields on a substrate.

As used herein, the term "pixel smear" refers to a measure of the spread of a pixel along an axis due to movement of an imaged object during image capture. A high amount of pixel smear will generate an image that is less sharp and has a higher amount of blur. In some embodiments, pixel smear is generated due to velocity fluctuations that are not compensated for in the optical path or in the movement of one or more tracking mirrors. Provided herein, in some embodiments, are devices and methods for capturing an image of a continuously moving substrate on a moveable stage with velocity fluctuations wherein the amount of pixel smear along the primary axis of movement of the substrate is mitigated by the rotation of one or more tracking mirrors along the optical path.

As used herein, the term "logic" refers to a set of instructions which, when executed by one or more processors (e.g., CPUs) of one or more computing devices, are operative to perform one or more functionalities and/or to return data in the form of one or more results or of input data that is used by other logic elements and/or by elements that control the operation of mechanical devices (e.g., such as servos and the like). In various embodiments and implementations, any given logic may be implemented as one or more software components that are executable by one or more processors (e.g., CPUs), as one or more hardware components such as Application-Specific Integrated Circuits (ASICs) and/or Field-Programmable Gate Arrays (FPGAs), or as any combination of one or more software components and one or more hardware components. The software component(s) of any particular logic may be implemented, without limitation, as a standalone software application, as a client in a client-server system, as a server in a client-server system, as one or more software modules, as one or more libraries of functions, and as one or more static and/or dynamically-linked libraries. During execution, the instructions of any particular logic may be embodied as one or more computer processes, threads, fibers, and any other suitable run-time entities that can be instantiated in the hardware of one or more computing devices and can be allocated computing resources that may include, without limitation, memory, CPU time, storage space, and network bandwidth.

Optical Scanning System and Methods of Use

Provided herein is a lightweight, cost-effective system for high frame rate image capture of portions or fields of a substrate with a high sensitivity while the substrate is moving on a moveable stage. This optical scanning system is capable of high speed, single molecule, single-fluor imaging, which to date has only been provided by heavy and expensive systems requiring precise control of stage movement, or through slower step and repeat optical scanning systems. The optical scanning system provided herein can be used as an image on the fly system (continuously moving stage) by using scanning optics which compensate for stage velocities that vary by 1% to 10% (typically resulting in image blur of at least several pixels). This compensation can result in an image equivalent of a tracked staged velocity with fluctuations less than 0.1% or a pixel smear of an image of no more than +/−1 pixel. Therefore, the scanning optics disclosed herein provide a system to compensate for velocity error (i.e., velocity fluctuations), such as localized accelerations and decelerations of a moveable stage or substrate, to provide a stabilized image field to a camera during imaging of a continuously moving moveable stage to reduce pixel smear.

The optical scanning system disclosed herein uses rotateable scanning optics and a control system to stabilize an optical path between a substrate and a detector while a substrate is in motion. The rotateable scanning optics rotate in response to stage velocity and stage velocity fluctuations (or to substrate velocity and substrate velocity fluctuations). Scanning optics provided by one embodiment of an optical scanning system with dual tracking mirrors are shown in FIG. 1. In this embodiment, the optical scanning system comprises a moveable stage 110 configured to move a mounted substrate 120 along an axis. The substrate 120 comprises one or more fields 121 that are individually imaged by the optical scanning system as the stage is continuously moving. The substrate is illuminated by an illumination mechanism (not shown), and light from the substrate travels along an optical path through the objective lens 130. The image of the moving substrate is stabilized with respect to an image sensor by a velocity tracking mirror 140 and an acceleration tracking mirror 150. An image of the field 121 is captured by a camera 160 comprising an image sensor. The velocity tracking mirror 140 is configured to rotate about an axis parallel to the plane of the image field. The rotation of the velocity tracking mirror 140 adjusts the optical path to stabilize the image of a field moving at a predetermined velocity during an image capture by the camera 160. The acceleration tracking mirror 150 is configured to rotate about an axis parallel to the plane of the image field. The acceleration tracking mirror 150 rotates as a function of velocity fluctuations (i.e., accelerations) of the moving stage or substrate. This rotation adjusts the optical path to stabilize an image by compensating for velocity fluctuations in the movement of the stage and/or substrate along an axis.

The optical scanning system in several embodiments is configured to image a continuously moving object, such as a substrate mounted on a moveable stage, in a scanning fashion. In such embodiments, a substrate is typically mounted (or otherwise placed) on a moveable stage that is coupled to one or more mechanisms (e.g., motors or other actuators) that can continuously move the substrate under an objective lens while a camera captures an image of a field of the substrate. The moveable stage is configured and operative to move the substrate along a direction that is normal to the optical axis of the objective lens. In some embodiments, the axis of movement of the moveable stage is orthogonal to the operation of autofocus-types of mechanisms, which generally move an imaged object and/or an objective along the optical axis of the objective lens.

In various embodiments, the velocity of the moveable stage may be in a range from 0.1 mm per second to 1000 mm per second (or greater). In some embodiments, the velocity of the moveable stage may be in a range from 10 mm per second to 100 mm per second. In some embodiments the moveable stage (and therefore the substrate mounted thereon) can be configured to move at a constant velocity, although the stage is still subject to velocity fluctuation errors that are compensated for by the optical systems provided herein. In some embodiments, the moveable stage moves at a velocity of 10 to 50 mm per second. In some embodiments, the velocity of the moveable stage is about 25 mm per second. In other embodiments, the moveable stage can be configured to move with non-constant velocity. This non-constant velocity can also be subject to fluctuation errors that are compensated for by the optical systems provided herein.

In some embodiments, mechanisms may be used to facilitate the motion of the moveable stage at a given desired velocity. Such mechanisms may comprise one or more components that cause motion (e.g., such as linear motors, lead screws, screw motors, speed screws, etc.) and one or more components (e.g., such as various types of bearings) that reduce friction.

For example, in some embodiments, a moveable stage may use metal bearings (e.g., such as ball bearings, cylinder bearings, cross-roller ball bearings, etc.) that have repeatability of several microns to facilitate motion of the moveable stage at a given desired velocity. Repeatability is fundamentally the effect of rolling a metal bearing in oil—as the metal bearing rolls it bounces, and such bouncing introduces jitter in the motion of the object that is being moved on the bearings. The "repeatability" of such motion can be uniform only above a certain range because any two metal bearings can bounce in the same way only within a certain tolerance. Thus, embodiments that use ball bearings typically have greater velocity fluctuations, and thus introduce image blur (e.g., pixel smear). However, stages using ball bearings provide several advantages, including that they are lighter, smaller, and cheaper than comparable air bearing stages. Thus, provided herein according to some embodiments are improved scanning optics to reduce image blur or pixel smear due to moveable stage velocity fluctuations, including stages with ball bearings or other components that provide motion subject to some velocity fluctuations.

In some embodiments, the velocity of the moveable stage fluctuates from the intended velocity by more than 0.1% during continuous optical scanning. In some embodiments, the velocity of the moveable stage fluctuates from the intended velocity by more than 0.5% during continuous optical scanning. In some embodiments, the velocity of the moveable stage fluctuates by between 0.1% and 1% during continuous optical scanning. In some embodiments, the optical scanning system provided herein reduces an image blur or pixel smear from a moveable stage with a velocity fluctuation of between 0.1% and 1% to less than 0.1%. In some embodiments, the pixel smear for a stabilized image is less than +/−1 pixel. In some embodiments, the moveable stage is configured to move a substrate in a continuous motion in a first known lateral direction with respect to the objective lens while a camera with a two dimensional full-frame electronic sensor produces the two-dimensional image. In some embodiments, the moveable stage is configured to move in a continuous serpentine fashion to image a plurality of rows or columns of fields on a substrate.

In some embodiments, a substrate is mounted (or otherwise placed) on a moveable stage. In some embodiments, the substrate comprises an array having target biomolecules disposed thereon. In some embodiments, the substrate comprises a multitude of distinct features that are targets for imaging. e.g., such as array chips. In some embodiments, the substrate comprises a randomly positioned array of targets for imaging.

In some embodiments, the substrate comprises a multitude of distinct features that are targets for imaging. For example, in some embodiments a substrate comprises a non-planar structure with a surface, such as a bead or a well, to which target biomolecules have been attached as the target features. In some embodiments, a substrate comprises an array chip. In some embodiments, the array chip is a solid phase support having a surface, e.g., a planar or substantially planar surface, that carries attachment sites to which biomolecules are attached as the target features. In some embodiments, the attachment sites on the array chip may be arranged in an ordered pattern or in random fashion. In some embodiments, the attachment sites are configured to have dimensions suitable for the attachment of target biomolecules. An attachment site is thus spatially defined and is not overlapping with other sites; that is, the attachment sites are spatially discrete on the array chip. When attached to the attachment sites, the biomolecules may be covalently or non-covalently bound to the array chip.

In some embodiments, the substrate is a biochip. In some embodiments, the biochip comprises high throughput microfluidics. In some embodiments, the biochip comprises biomolecules for detection of single molecules from a sample. In some embodiments, the substrate comprises an array having target nucleic acids disposed thereon. In another embodiment, the substrate comprises a multitude of distinct features that are targets for imaging.

In some embodiments the attachment sites on a substrate are divided into fields that are each imaged separately. A typical substrate may be divided into hundreds or thousands of fields that are arranged in a rectangular pattern of rows and columns. (For example, the rows and columns of fields may include track regions that are aligned substantially along a horizontal dimension and a vertical dimension, respectively).

In such embodiments, the techniques described herein provide for scanning and imaging a substrate field by field. In one example, an optical scanning system images a substrate in a scanning fashion (as described herein) while the moveable stage is moving the substrate along a y-direction in a plane and/or axis that is substantially normal to the optical axis of the objective lens. In this example, the optical scanning system ceases imaging when the end of the column of field(s) being imaged is reached in order to allow the moveable stage to position the substrate for imaging of the next column of field(s). In another example, an optical scanning system images a substrate in a scanning fashion (as described herein) while the moveable stage is moving the substrate backward and forward in a serpentine fashion (e.g., along a y-direction) in a plane that is substantially normal to the optical axis of the objective lens. In this example, the optical scanning system images a column of field(s) while the moveable stage is moving the substrate in one direction and then images the next/adjacent column of field(s) while the moveable stage is moving/returning the substrate in the opposite direction, e.g., the optical scanning system images the substrate by effectively traversing the columns of fields in a continuous serpentine fashion.

The objective lens of the optical scanning system is configured and operative to image a substrate or a portion thereof onto the camera. In some embodiments, the objective lens is an element or group of elements, in an optical scanning system, that comprises one or more lenses and is configured and operative to magnify an electromagnetic (e.g., such as optical) signal. In some embodiments, an objective lens has a large numerical aperture (NA) (e.g., NA in a range between 0.6 and 1.5) and performs imaging via air immersion (e.g., such as water, oil, or other immersion fluids). In various embodiments, an objective lens may have a focal length in the range from 2 mm to 40 mm. The objective lens can be an off-the-shelf microscope objective or a custom-designed, multi-element optical component. In some embodiments, the objective lens is configured to image at least a two-dimensional portion of a substrate onto the two dimensional full-frame electronic sensor of the camera to produce a two-dimensional image.

The magnification of an objective lens is the ratio of the size of an image space pixel (i.e., a camera pixel) to the actual size of the object space area that corresponds to the image space pixel as observed by the camera. For example, a magnification of 16× allows a camera using 8 μm pixels to observe 500 nm object space pixels. In some embodiments, the objective lens has a magnification from 4× to 100×. In some embodiments, the objective lens has magnification of 20× to 50×. In some embodiments, the objective lens has a magnification of 40×.

In some embodiments, the objective lens is operably connected to an electrical motor for positioning the objective lens to allow auto-focusing. In some embodiments, the device comprises a focusing sensor. In some embodiments, the device comprises an array of focusing sensors.

In some embodiments, auto-focus mechanisms used are based on optical sensing methods. In some embodiments, auto-focusing is performed by image content analysis. In some embodiments, autofocusing is performed by obtaining multiple images of the substrate at multiple focal distances, determining an optimal focal distance for each of the images, and using a feedback loop to adjust the focal distance.

Autofocusing can be performed by directing a laser beam at the substrate, measuring a reflection of the laser beam off the substrate to provide a reference point, and using a feedback loop to adjust the focal distance. In some embodiments, non-optical types of non-contact position sensors are used. These sensors are capable of making position readings with high bandwidth and a tracking precision of 0.1 μm or less. In some embodiments, capacitive position sensors may be used (see, e.g., US 2002/0001403, whose disclosure is incorporated herein by reference).

In some embodiments, autofocus of the objective lens is achieved in less than 100 ms. In some embodiments, the range of autofocus provided by the device is +/−200 μm.

In some embodiments, the optical scanning device comprises an active autofocus system that measures distance to the subject independently of the optical system, and subsequently adjusts the objective lens to correct focus. In some embodiments, a passive autofocus system that determines correct focus by performing passive analysis of the image that is entering the optical system is used. Passive autofocusing can be achieved, for example, by phase detection or contrast measurement.

In some embodiments, the optical scanning system comprises a camera capable of capturing a 2-dimensional still image of a field of the substrate while the substrate is being moved by the moveable stage. In some embodiments, the optical scanning system comprises a full-frame camera. In some embodiments, the full-frame camera is a Complementary Metal-Oxide Semiconductor (CMOS) camera. These full frame cameras have high speed, high resolution, and low cost. Furthermore, they are compatible with the optical scanning system for capturing an image of a continuously moving substrate at a high resolution. In some embodiments, the camera is a scientific CMOS (sCMOS) camera. In some embodiments, the camera is a non-CMOS camera capable of operating in full-frame mode.

The optical scanning systems described herein are configured to use fast cameras in conjunction with a scanning optics (e.g., single mirror or dual mirror embodiments) in order to achieve continuous exposure of a still image while the substrate being imaged is moving. In some embodiments, the size (length and/or width) of a camera pixel is in a range from 5 μm to 10 μm, preferably but not exclusively in the range of 6-8 μm. In some embodiments, the size of a camera pixel is 6.5 μm. In some embodiments, the camera comprises an imaging sensor on the range of 15×15 mm to 10×10 mm.

In various embodiments, the optical scanning systems described herein are configured to scan a continuously moving substrate (e.g., such as an array chip) by using fast cameras that do not move the image through the camera, e.g., such as non-TDI cameras and other cameras (including TDI cameras) that operate in full-frame 2D mode. CMOS cameras are an example class of such cameras. CMOS cameras typically use an active-pixel sensor (APS) that is an image sensor comprising of an integrated circuit containing an array of pixels, where each pixel includes a photodetector and an active amplifier.

A high-speed camera may be defined in terms of the number of pixels that the camera can expose in a unit of time. For example, the speed of the camera may be defined by the mathematical product of the number of pixels in the field of view and the frames per second that the camera can take. Thus, a camera with a field of view of 5.5 megapixels (e.g., a view of 2560 pixels by 2160 pixels) running at 100 frames per second (fps) would be able to expose 550 megapixels per second; thus, such camera is termed herein as a "550" megapixel camera. Examples of such cameras include, without limitation, CMOS, sCMOS, and similar cameras. In various embodiments, the optical scanning systems described herein may use cameras in the range from 10 megapixels to 2500 megapixels. In some embodiments, the camera comprises a 2-dimensional, full frame electronic sensor.

Scanning optics described herein as part of the optical scanning system can include single tracking mirror and dual tracking mirror embodiments having one or more rotatable mirrors affixed along an optical path of the system between the imaged object and the camera. In a dual tracking mirror embodiment, two sets of scanning optics are used, each able to move in concert to track the motion of a moveable stage along an an axis during imaging. A first scanning optic (e.g., a velocity tracking mirror) is used to track the movement of a stage at an anticipated velocity or velocity pattern to enable imaging of a field by a camera while the field is in motion. A second scanning optic (e.g., an acceleration tracking mirror) is used to compensate for local stage accelerations that could result in unacceptable pixel smear, thus stabilizing the image. In single tracking mirror embodiments, a single set of scanning optics is used both to track the movement of a stage at an anticipated velocity or velocity pattern and to compensate for local stage accelerations (i.e. velocity fluctuations) that could result in unacceptable pixel smear, thus stabilizing the image. For single tracking mirror embodiments, a single set of scanning optics compensates for all stage motion including velocity and acceleration (or velocity fluctuations). In some embodiments, the single set of scanning optics includes a motion tracking mirror to indicate its compensation for both constant or anticipated velocity or velocity patterns and measured or predetermined velocity fluctuations (accelerations).

In some embodiments, the movement of a tracking mirror in response to velocity fluctuations of the moveable stage is based on a feedback control mechanism. In some embodiments, the feedback control mechanism comprises a device to measure position of a substrate over time, such as an encoder. In some embodiments, the movement of a mirror in response to velocity fluctuations is based on predetermined velocity fluctuations for a moveable stage. In some embodiments, all rotatable scanning optics are positioned along an optical path before any splitter used to split an image to multiple cameras.

In some embodiments, provided herein are optical scanning devices comprising a velocity tracking mirror configured to rotate to allow a camera sensor to image a field of a substrate moving along an axis on a moveable stage. The velocity tracking mirror is operably mounted to the device to reflect light along an optical path from the objective lens to the camera.

In order to maintain a still image of a moving substrate, the velocity tracking mirror is configured and operative to move in coordination with the moveable stage, while the moveable stage moves the substrate in the same specified direction, in order to reflect light from the objective lens to the camera. Thus, the velocity tracking mirror can be operably mounted to the device to rotate about a fixed axis. In some embodiments, the fixed axis is parallel to the plane of the 2-dimensional substrate image. In some embodiments, the fixed axis is orthogonal to the optical path. Thus, the velocity tracking mirror is configured and operative to perform an angular motion that allows the camera to acquire a still image of a field of the substrate through an objective lens while the substrate is being moved by the moveable stage.

The velocity tracking mirror can be operably coupled to an electrical motor to effect rotation of the velocity tracking mirror. In preferred embodiments, the electrical motor operably coupled to the velocity tracking mirror is a galvanometer, although other types of electrical motors may be used. An example of a suitable galvanometer is a Nutfield QS-7 OPD Galvanometer Scanner (Nutfield Technology). In some embodiments, other mechanisms to actuate the velocity tracking mirror, such as those based on hydraulics, pneumatics, or magnetic principles, may also be used. In some embodiments, the electrical motor is operatively coupled to the velocity tracking mirror and is operative to angularly move the velocity tracking mirror in coordination with the moveable stage, while the moveable stage moves the substrate, in order to keep an image of the substrate (or a field) still with respect to the camera while the image is being acquired through the objective lens.

The movement of the velocity tracking mirror can be coordinated through a controller module configured to send a driving signal to the electrical motor operably connected to the velocity tracking mirror. The controller module can include a motion controller component to generate a desired output or motion profile and a drive or amplifier component to transform the control signal from the motion controller into an electrical signal or a drive signal that actuates the electrical motor.

In some embodiments, the velocity tracking mirror has an angular range of rotation of about 60 degrees, 50 degrees, 40 degrees, 30 degrees, 20 degrees, 15 degrees, 10 degrees or 5 degrees. In some preferred embodiments, the velocity tracking mirror has an angular range of rotation of about 3 degrees, 2 degrees, 1 degree, ½ degree, ¼ degree, or 1/10 degree.

In an optical scanning system that uses a velocity tracking mirror to image a moving substrate, the mirror angle is adjusted with time so that a camera can view a fixed area on a moving substrate. This is referred to as the "forward scan" time. The velocity tracking mirror can then quickly rotate to return to its initial position. This is referred to as a "fly-back" time or "backscan" time. During the fly-back time, the image projected onto the camera is not stable.

Figure 2:
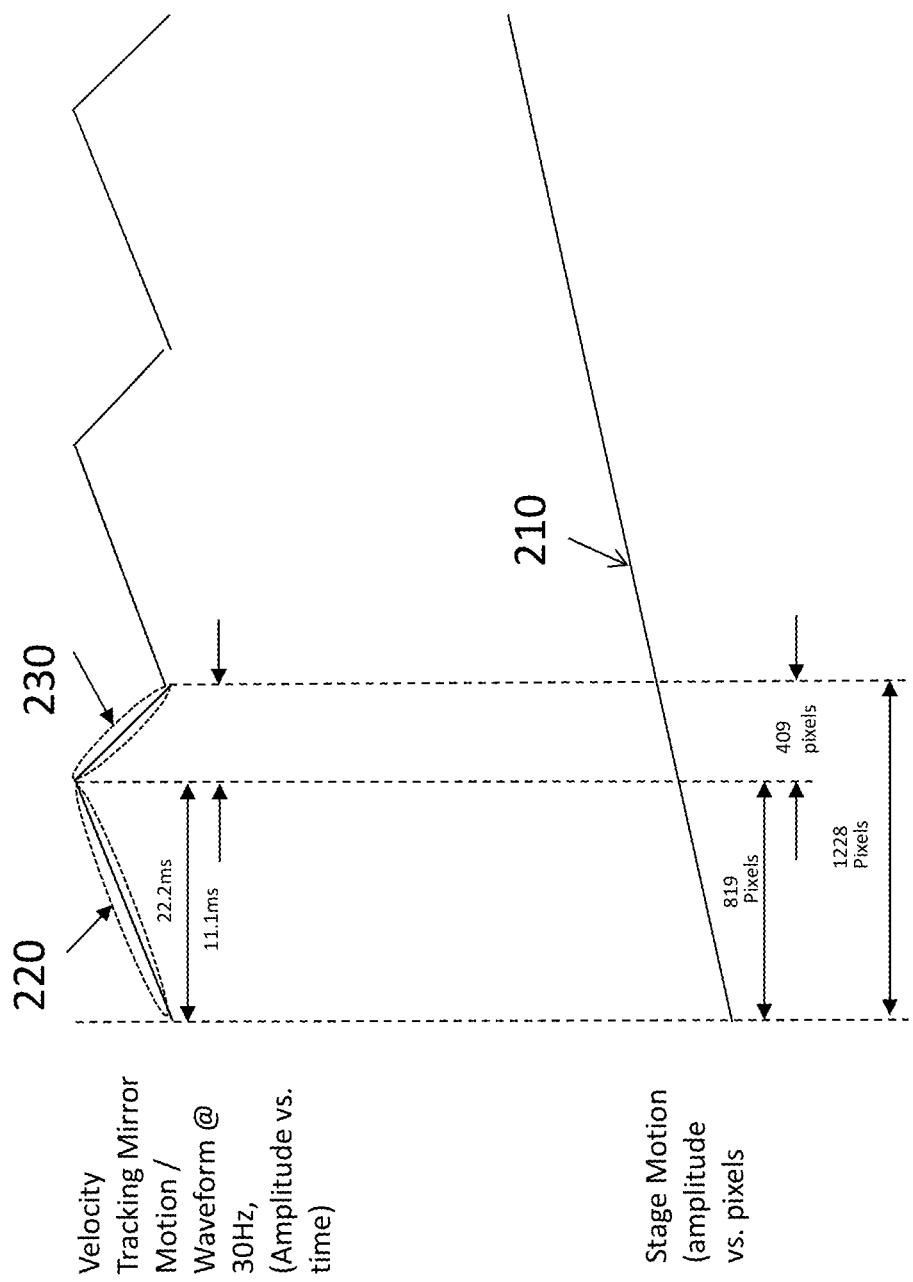
FIG. 2 is a representation of a sawtooth waveform to control the motion of a moving stage tracking mirror, such as a velocity tracking mirror, and its correlation to the change in position of a moveable stage along an axis over time according to an embodiment.

FIG. 2 illustrates a diagram of velocity tracking mirror angular movement and timing according to an example embodiment. In operation, the objective lens is focused on a substrate (e.g., an array chip) that is moving along an axis during imaging. FIG. 2 shows movement of the stage over time 210. During this movement, the velocity tracking mirror rotates from its initial position to its end position to track the movement of the substrate, which is represented as the forward scan time 220. During a single forward scan, a portion of the substrate is imaged, which is referred to herein as a field. The rotation of the velocity tracking mirror allows imaging of the substrate portion corresponding to the field by the camera during the exposure time, thereby allowing sufficient exposure onto the camera sensor. Any remaining movement of the field with respect to the camera can be due to velocity fluctuations, or deviations of the substrate velocity from the anticipated velocity. When the velocity tracking mirror reaches its extreme end position, it then moves back to its initial position in preparation for a new scan, which is represented by the waveform or motion of the mirror at 230 (fly-back time). Still images of the substrate are not acquired during the fly-back time intervals. The forward scan and fly-back motions of the velocity tracking mirror are represented as a sawtooth waveform (FIG. 2), which reflects both the motion of the velocity tracking mirror during scanning and flyback and the driving signal sent to an electrical motor operably connected to the velocity tracking mirror to actuate the mirror.

Figure 3:
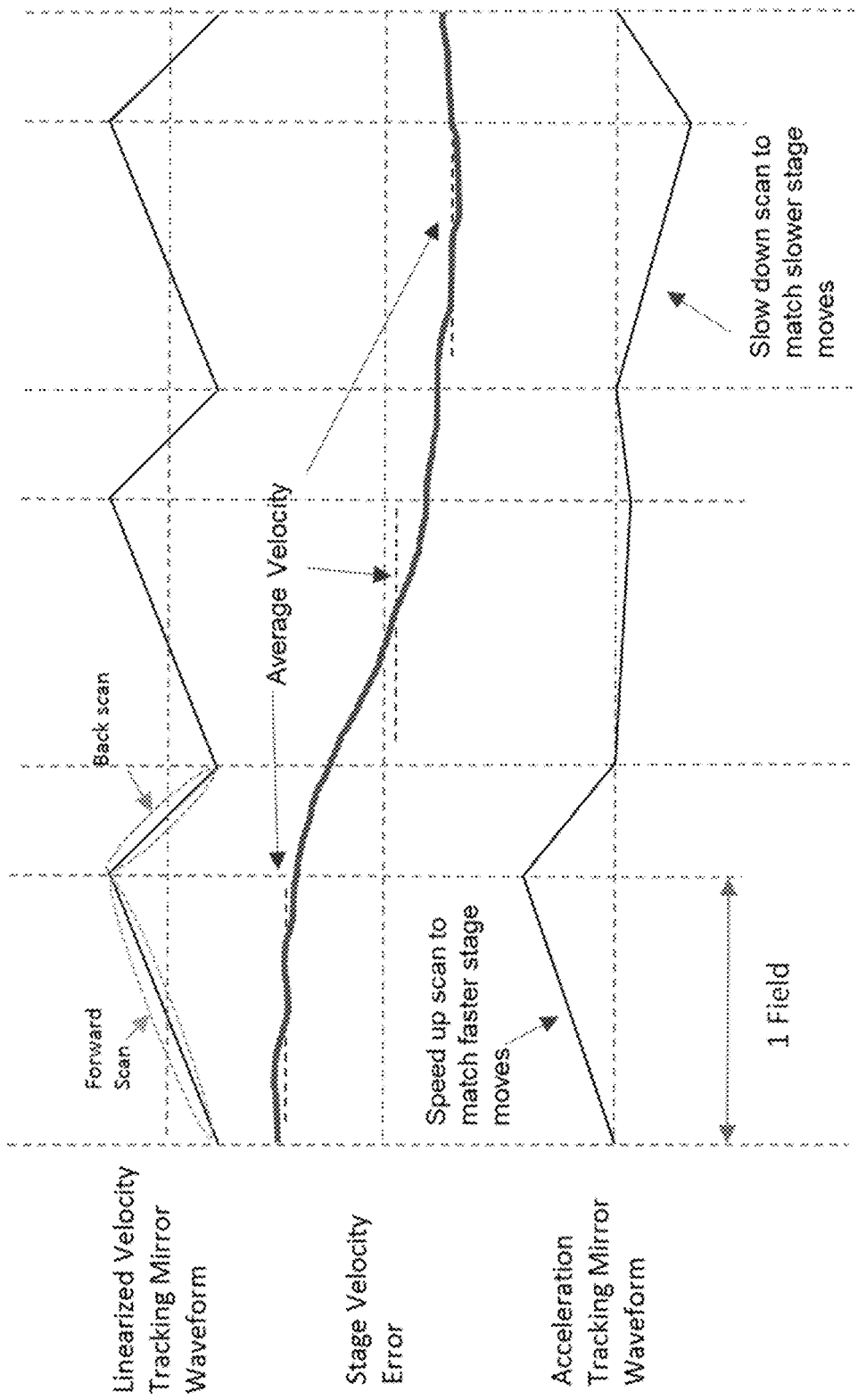
FIG. 3 provides an example of waveforms that can be used to generate driving signals for a velocity tracking mirror and an acceleration tracking mirror (in a dual mirror embodiment) to stabilize an image of a moving substrate based on a measured or anticipated stage velocity error and an anticipated stage velocity.

An embodiment of a sawtooth waveform to drive the mirror (including a forward scan and backscan segments) is shown in FIGS. 2 and 3. In some embodiments, the velocity tracking mirror may have a non-linear response over segments of it's range of motion. In this case, the velocity tracking mirror response may be linearized by adjusting the waveform or driving signal so that you to linearize the response from the velocity tracking mirror.

In some embodiments, the velocity tracking mirror is operably coupled to an electrical motor to effect rotation of the acceleration tracking mirror. In preferred embodiments, the electrical motor operably coupled to the velocity tracking mirror is a galvanometer, or electric coil in a magnetic field that moves in response to an electrical current. In some embodiments, other mechanisms to provide actuation of the velocity tracking mirror, such as those based on hydraulics, pneumatics, or magnetic principles, may also be used. In some embodiments, the electrical motor operatively coupled to the velocity tracking mirror is operative to generate angular motion of the velocity tracking mirror as a function of a velocity of the moveable stage or substrate.

In some embodiments, the movement of the velocity tracking mirror is coordinated through a controller module configured to send a driving signal to the electrical motor operably coupled with the velocity tracking mirror. The controller module can include a motion controller component to generate a desired output or motion profile and a drive or amplifier component to transform the control signal from the motion controller into energy that is presented to the electrical motor as an electrical signal or a drive signal.

In some embodiments, the driving signal or electrical signal sent to the electrical motor operably coupled with the velocity tracking mirror can be a linearized velocity tracking error waveform defined as a function of $G(\theta,\omega,\varepsilon(\theta))$, where G is a modified triangle wave with $\theta$=angular position, $\omega$=frequency, and $\varepsilon(\theta)$=amplitude.

The movement of a tracking mirror can be characterized by its duty cycle, defined as the portion of time the tracking mirror is operably moving in the forward scan motion to allow active imaging of the substrate. For example, if the tracking mirror tracks the substrate to allow imaging by the camera during at least 90% of the tracking mirror cycle (e.g., when the tracking mirror fly-back time is equal to or less than 10% of the cycle), then this technique allows the camera to operate with at least a ~90% overall readout efficiency.

In some embodiments, such as fluorescence imaging where longer exposure times may be needed, the scan time interval, during which an image is collected by the camera, must be long enough to build up adequate signal-to-noise ratios as fluorescence imaging light levels are typically very weak.

The duty cycle is also impacted by the speed with which the tracking mirror returns to its initial position. This fly-back time interval can be configured to be only a small fraction of the tracking mirror cycle, thus maximizing the duty cycle. For better efficiency, the amount of time spent by a tracking mirror on each imaged area is made commensurate with the camera's frame rate, thereby allowing sufficient time to expose an image of each field onto the camera.

In some embodiments, the duty cycle is greater than 60%. In some embodiments, the duty cycle is from 60% to 90%. In some embodiments, the duty cycle of the image capture is at least 1%, 2%, 3%, 4%, 5%, 6%, 7%, 8%, 9% or 10%. In some embodiments, the duty cycle can be as low as 10%, or can be in the range of 20%, 30%, 40%, 50%, 60%, 70%, 80% or 90%. In some embodiments, these duty cycles are achieved with an imaging frequency of from 30 to 200 Hz. In some embodiments, these duty cycles are achieved with an imaging frequency of from 30 to 40 Hz. In some embodiments, these duty cycles are achieved with an imaging frequency of 30 Hz, 35 Hz, 40 Hz, 45 Hz, or 50 Hz.

During the fly-back time intervals, the optical scanning system should cease imaging because the image being acquired is not stable. Thus, in various embodiments various mechanisms can be used to prevent image exposure to the camera during the fly-back time intervals. For example, in some embodiments an acousto-optic modulator (AOM) switch (or other type of fast switch) may be used to turn on and off the illumination light that is incident onto the substrate being imaged. In other embodiments, a suitable aperture can be placed in the optical path of the illumination light, where the illumination light is allowed to overscan but the aperture prevents the light from illuminating the substrate during the fly-back time intervals by blocking out the light outside of the field of view. In yet other embodiments, a suitable shutter can be placed in the optical path of the illumination light, where the shutter is kept open during exposure intervals and is closed during the tracking mirror fly-back time intervals.

In dual tracking mirror embodiments, the optical scanning device further comprises an acceleration tracking mirror configured and operative to provide offset corrections to an optical path to stabilize the transmission of light from a substrate to the camera during imaging of the substrate (or a portion thereof). The offset corrections are a function of velocity fluctuations in the movement of the moveable stage along an axis as compared to the velocity tracked by the velocity tracking mirror. These velocity fluctuations can impact the accuracy of tracking of the moveable stage by the velocity tracking mirror and result in an image with unacceptable pixel smear. The rotation of the acceleration tracking mirror, as provided herein, stabilizes the image of the field captured by the camera to reduce pixel smear from velocity fluctuations of the stage or substrate.

FIG. 3 provides one example of an acceleration tracking mirror waveform generated in response to an average stage velocity error for a field. When the stage velocity has a positive error, an acceleration tracking mirror waveform is generated to track the additional velocity of the stage. Conversely, when the stage velocity has a negative velocity error, an acceleration tracking waveform is generated to track the slower velocity of the stage (i.e., it rotates in the opposite direction as a positive velocity error). In some embodiments, the acceleration tracking mirror waveform is generated and converted to a driving signal immediately after sensing the velocity error. In some embodiments, the acceleration tracking mirror waveform is generated based on an average measurement of velocity during imaging of a field n-1, and the driving signal is generated from this waveform to drive movement of the acceleration tracking mirror during imaging of field n.

Stage velocity error can be modeled as a function of amplitude (A), stage position (x), and time (t), to give the following function:

$$F(A,x,t)=A(x)*\mathrm{Err}(x,t)$$

In some embodiments, the electrical signal or driving signal (D) to control movement of an electrical motor operably connected to the acceleration tracking mirror can be determined based on the stage velocity error by a function represented as follows:

$$D(F,C,x,E)=F(A,x,t)_y*C*x+E,$$

where C is a scaling factor, x=stage position and E is an offset. $F(A,x,t)_y$ is the average value of $F(A,x,t)$ over the ramp range=y, or over a prior field, as described herein. A function to smooth discontinuities can also be used to generate the acceleration tracking mirror driving signal.

In some embodiments, the acceleration tracking mirror is operably coupled to an electrical motor to effect rotation of the acceleration tracking mirror. In preferred embodiments, the electrical motor operably coupled to the acceleration tracking mirror is a piezoelectric actuator, although other types of electrical motors may be used. In some embodiments, other mechanisms to provide actuation of the acceleration tracking mirror, such as those based on hydraulics, pneumatics, or magnetic principles, may also be used. In some embodiments, the electrical motor operatively coupled to the acceleration tracking mirror is operative to generate angular motion of the acceleration tracking mirror as a function of fluctuations in the velocity of the moveable stage to compensate for velocity fluctuations during imaging.

In some embodiments, the movement of the acceleration tracking mirror is coordinated through a controller module configured to send a driving signal to an electrical motor operably connected to the acceleration tracking mirror. The controller module can include a motion controller component to generate a desired output or motion profile and a drive or amplifier component to transform the control signal from the motion controller into energy that is presented to the electrical motor as an electrical signal or a drive signal.

Since the movement of the acceleration tracking mirror is a function of fluctuations in velocity of the moveable stage, the controller module can further comprise a position, velocity or acceleration sensor. This sensor can act as a type of feedback sensor that determines information about the position and/or motion of the substrate or moveable stage. In some embodiments, the sensor comprises an encoder (e.g., a linear encoder) or an interferometer operably mounted to the scanning device. In some embodiments, the encoder is a non-interferometric encoder. In some embodiments, an accelerometer could be used to determine changes in velocity. In some embodiments, the sensor is a component that provides information from a velocity fluctuation table that includes anticipated velocity fluctuation values for a stage to incorporate into the driving signal for the electrical motor operably coupled to the acceleration tracking mirror.

An encoder can be a sensor, transducer or readhead paired with a scale that encodes position. In some embodiments, the sensor reads the scale (e.g., encoder counts) in order to convert the encoded position into an analog or digital signal, which can then be decoded into position by a digital readout (DRO) or motion controller. Thus, in some embodiments, the position sensor (including position, velocity, and/or acceleration sensors) is a linear encoder that interfaces with encoder counts (or another scale) on the substrate or moveable stage. In some embodiments, the encoder counts on the substrate are positioned at a distance of 10 µm, 5 µm, 2 µm, 1 µm, or 500 nm or less between each encoder count. In some embodiments, the resolution of position detectable by the encoder is 1 nm or less. This can be done for example, using interpolaton between lines on a substrate or between encoder counts. The spacing between encoder counts can correlate with stage scan speed and frequency of position measurement.

In some embodiments, the scale used by an encoder, such as a linear encoder, can be optical, magnetic, capacitive, inductive, based on eddy current. In some embodiments, position detection can be done without a scale on the substrate or moveable stage, for example, by using an optical image sensor based on an image correlation method.

The position measurements from a substrate or stage position or motion sensor are used to provide a set of data that represents the measured velocity of the substrate or moveable stage. The measured velocity can be compared with an anticipated velocity to determine velocity fluctuations in the stage. These velocity fluctuations can then be translated into an electrical signal (e.g., a driving signal) which effects controlled movement of an electrical motor operably connected to the acceleration tracking mirror. The controlled movement of the acceleration tracking mirror adjusts the position of the optical path between the substrate and the camera to provide an image with increased stability, increased sharpness, and/or reduced blur or pixel smear.

An electrical motor can be selected on the basis of its ability to quickly respond to a driving signal comprising a correction term based on measured velocity fluctuations. To provide a quick response, in some embodiments, the electrical motor has a total angular range of rotation of less than one degree. In some embodiments, the electrical motor is a piezoelectric actuator or another motor with a similar response time to the correction signal. In some embodiments, the position sensor acquires position information at a rate of equal to or greater than 500 Hz, 1 kHz, 2 kHz, 3 kHz, 4 kHz, 5 kHz, 10 kHz, 20 kHz, 50 kHz, 100 kHz and 250 kHz. In certain embodiments, a higher frequency of position detection, e.g., 5 kHz or more, allows a more precise measurement of the stage to increase the resolution of velocity fluctuation and therefore provide a sharper image. However, lower frequencies may be used that are sufficient to provide correction to prevent a pixel smear of greater than two pixels.

For example, in some embodiments an encoder provides substrate or stage position or motion measurement information to logic executing in a computing device, such as a motion controller, where the logic uses the measurement information to compute the necessary correction term for the direction of stage movement and to cause a servo mechanism, such as an electrical motor, to rotate the acceleration tracking mirror based on the computed correction term that is a function of velocity fluctuation of the moveable stage.

The determination of velocity fluctuation can be determined from two or more position measurements from the position sensor. In some embodiments, near instantaneous velocity can determined from the most recent 2 or 3 positions measured from the substrate.

In some embodiments, velocity fluctuation used to generate a driving signal is determined from a pre-calculated table. A velocity fluctuation may already be known for a stage, and can be recorded into a table which is accessed by the motion controller component. Thus, in these embodiments, the position sensor is a component of the controller module that provides data from a velocity fluctuation table to a motion controller.

By using an acceleration tracking mirror as described herein, an optical scanning system can use a camera that operates in a full-frame mode (e.g., such as a CMOS camera that does not operate in TDI mode) to acquire still images of a moving substrate within an accuracy of +/−one pixel. In some embodiments that are employed for biological imaging, e.g., DNA sequencing or other single molecule detection techniques, the extreme alignment accuracy requirements of fluorescence imaging may necessitate the use of at least one velocity and acceleration tracking mirror pair to correct for movement, including velocity fluctuations, of a substrate along an axis to remove nonlinearities in the motion of the moveable stage.

In some embodiments, tracking of the movement of the stage, including both a velocity of a stage and velocity fluctuations of the stage along an axis, is performed by a single tracking mirror (the single-mirror embodiment), referred to herein as a motion tracking mirror. In this embodiment, a single motion tracking mirror performs the functions of both the velocity and acceleration tracking mirrors described above. Therefore, in a single mirror embodiment, a drive signal is sent to an electrical motor operably coupled to the single motion tracking mirror that is a function of a predetermined stage velocity including both scanning and flyback waveforms (e.g., a sawtooth wave) and is also a function of velocity fluctuations of the stage or substrate, which can be predetermined or can be based on one or more measurements that provide information about the motion of the substrate or moveable stage to determine a velocity fluctuation of the stage or substrate.

Figure 4:
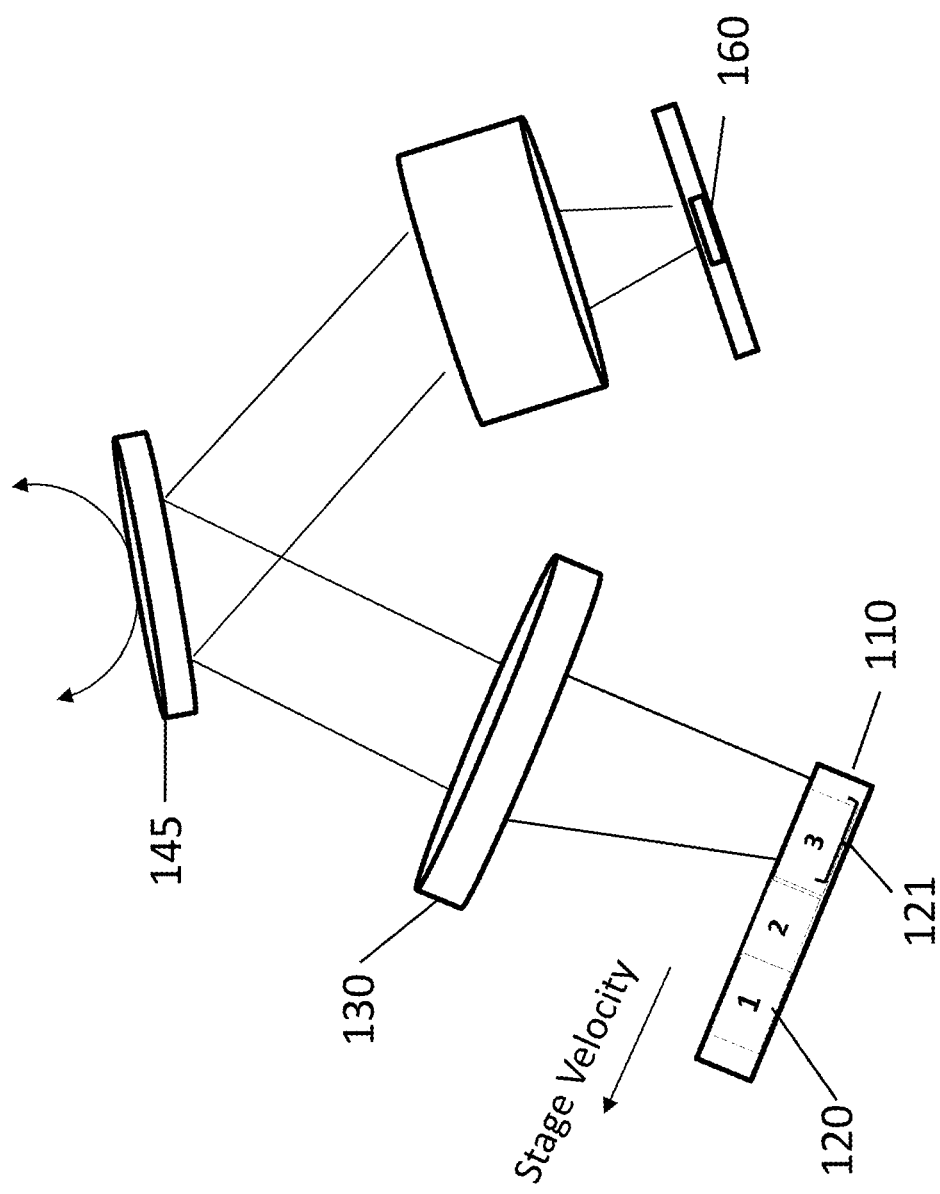
FIG. 4 is a diagram of components of an optical scanning device along an optical path from a substrate to a detector comprising a single motion tracking mirror (i.e., a single-mirror embodiment) according to an embodiment of the invention.

Scanning optics provided in a single mirror embodiment of the optical scanning system is shown in FIG. 4. In this embodiment, the optical scanning system comprises a moveable stage 110 configured to move a mounted substrate 120 along an axis. The substrate 120 comprises one or more fields 121 that are individually imaged by the optical scanning system as the stage is continuously moving. The substrate is illuminated by an illumination mechanism (not shown), and light from the substrate travels along an optical path through the objective lens 130. The image of the moving substrate is stabilized with respect to an image sensor by a motion tracking mirror 145. An image of the field 121 is captured by a camera 160 comprising an image sensor. The motion tracking mirror 145 is configured to rotate about an axis parallel to the plane of the image field. The rotation of the motion tracking mirror 145 adjusts the optical path to stabilize the image of a field during an image capture by the camera 160. Rotation of the motion tracking mirror 145 is a function of both a predetermined stage velocity and velocity fluctuations of the stage or substrate. Thus, the single-mirror embodiment of the optical scanning system provides a stabilized image with an improved sharpness or reduced pixel smear over a system that does not correct for stage velocity fluctuations while imaging a moving substrate.

A controller module configured to drive the movement of the single motion tracking mirror includes components of both a controller module operably connected to a velocity tracking mirror and components of a controller module operably connected to an acceleration tracking mirror, as described in the two-mirror embodiment above. Therefore, in some embodiments, the controller module comprises a motion controller component that generates a desired output or motion profile, a drive or amplifier component to transform the control signal from the motion controller into an electrical signal or drive signal. The controller module can also include a position, velocity, or acceleration sensor configured to determine the position or motion of the substrate or moveable stage, and to send this signal to the motion controller component to be used to generate the desired output or motion profile as a function of the information from the sensor. The motion controller component can then generate a motion profile for the single motion tracking mirror that is a function of both the constant or otherwise anticipated velocity of the substrate or stage (e.g., a sawtooth waveform) and velocity fluctuations determined from the signal from the sensor or that are predetermined for the stage. Thus, the sawtooth waveform used to track velocity can be modified according to a real time velocity measurement determined from a signal from a positional sensor or from predetermined velocity fluctuations.

Figure 5:
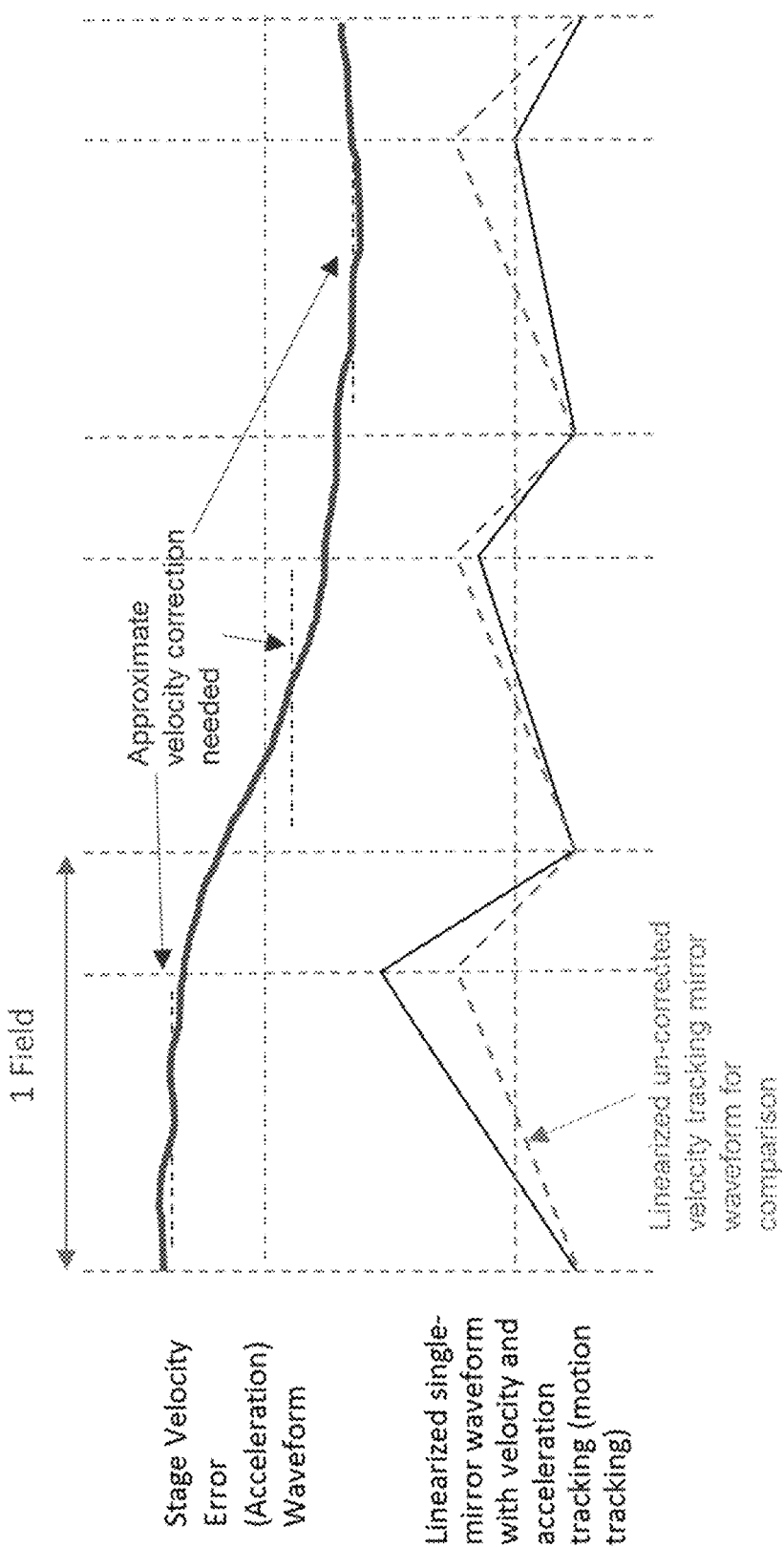
FIG. 5 provides an example of waveforms that can be used to generate driving signals for a motion tracking mirror (in a single mirror embodiment) to stabilize an image of a moving substrate based on a measured or anticipated stage velocity error and an anticipated stage velocity.

FIG. 5 provides an example stage velocity error waveform generated from data provided by a position, velocity or acceleration sensor. Also shown are approximate velocity corrections needed, otherwise known as the average velocity error for a field. The next waveform (solid line) shows a velocity tracking waveform modified by a correction term that is a function of an average velocity error (e.g., an average velocity error for a field). The dashed line represents a linearized, un-corrected motion tracking mirror waveform (similar to the waveform used to drive a velocity tracking mirror in the dual-mirror embodiment). When there is a positive velocity error, the slope of the waveform during scanning is increased, thereby increasing the speed of the rotation of the mirror to compensate for the velocity error. When there is a negative velocity error, the slope of the waveform is decreased, thereby decreasing the speed of the rotation of the mirror to compensate for the velocity error.

In some embodiments, the sensor determines an average velocity of the stage or substrate based on a plurality of measurements taken during imaging of a field. In some embodiments, the sensor is a position sensor. In some embodiments, the position sensor is an encoder (e.g., a linear encoder) or an interferometer operably mounted to the scanning device. The signal from the position sensor can be used to determine the average velocity of the moveable stage or substrate using two or more of the most recent positional measurements captured by the position sensor. In some embodiments, these measurements can be used to adjust the angle of the motion tracking mirror after sensing.

Figure 6:
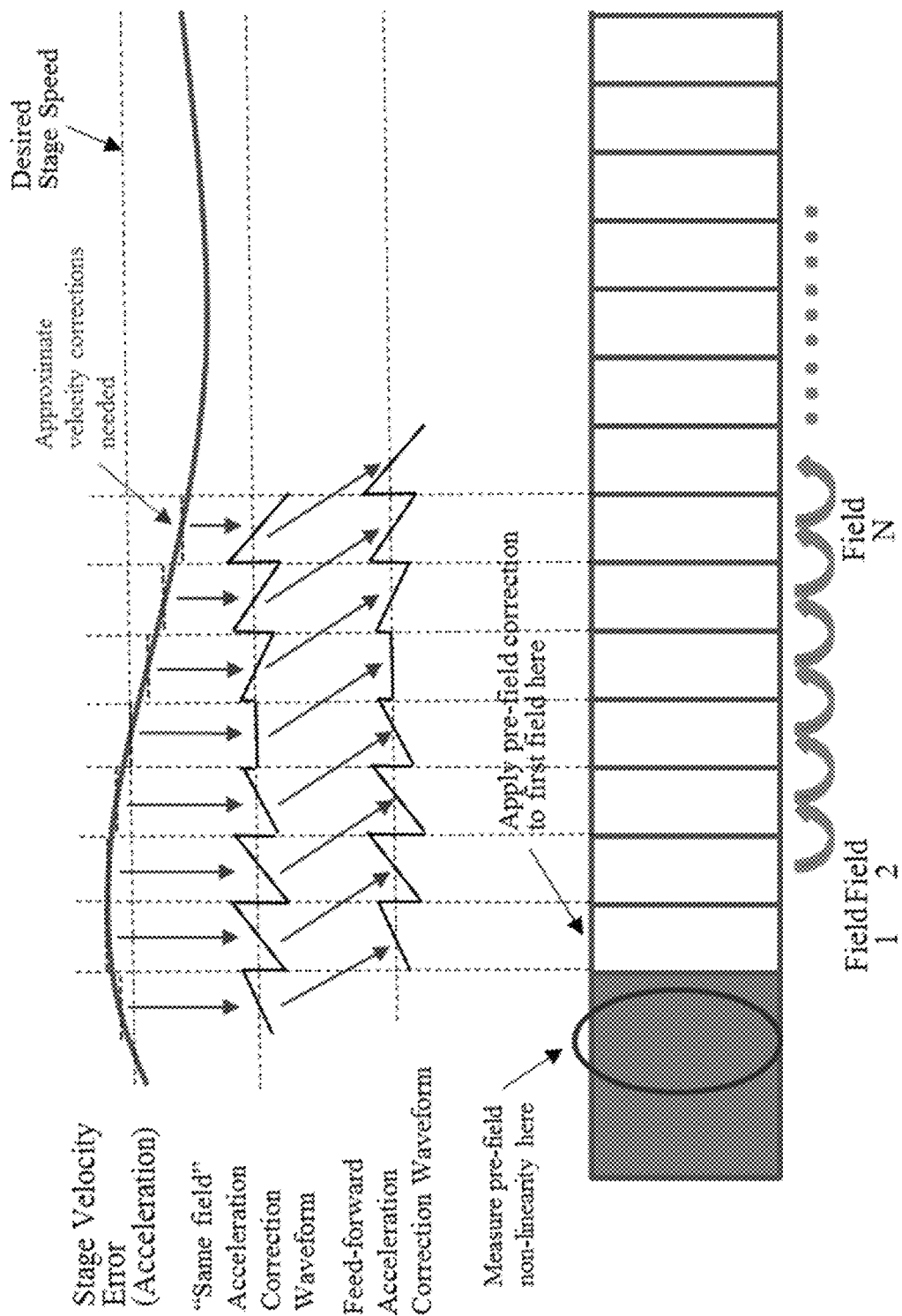
FIG. 6 provides a schematic of one possible implementation of a field level feed-forward mechanism to provide a correction term to adjust a drive signal provided to a mirror of the device capable of moving in response to velocity fluctuations of the substrate or moveable stage.

In some embodiments, the average velocity of a substrate or stage is determined over a field n−1 and is used to provide a correction term which is used for generating the motion profile of the motion tracking mirror for field n. This is known as the field level feed forward mechanism, as illustrated in FIG. 6. In some embodiments of the field level feed forward correction mechanism, the motion controller component generates a motion profile for movement of the motion tracking mirror (in the single mirror embodiment) or the acceleration tracking mirror (in the dual mirror embodiment) as a function of the average velocity of the previous imaged field. A field level feed-forward velocity tracking and correction mechanism is distinct from other types of correction, such as a scanline level feed forward mechanisms. Field-level feed forward corrections are advantageous in that they reduce the stringency of immediate signal processing while still providing sufficient correction information to generate an acceptably sharp image for monitoring information in single pixels (i.e., a pixel smear of no more than +/− one pixel). Some image blur or pixel smear may not be corrected by field level feed forward mechanisms, however, in some embodiments, such as in single molecule imaging applications (e.g., for biomolecular sensing), a pixel smear of up to +/−one pixel is acceptable, and field-level feed forward corrections can generate an acceptable smear when there is a velocity fluctuation from field n−1 to field n that is within an acceptable level (e.g., results in a pixel smear of no more than +/−one pixel).

Provided in FIG. 6 is a diagram of an embodiment of field level feed-forward correction. In this embodiment, velocity tracking measurements of a chip or stage are obtained to generate a mirror rotation drive signal that incorporates velocity fluctuations of the moving stage. Here, the stage begins moving, and positional information is obtained over time (or velocity information is obtained) to determine a pre-field non-linearity of the velocity of the stage (velocity fluctuations). When the first field is imaged, a driving signal that is a function of the average velocity measured in the pre-field stage is sent to the motion tracking tracking mirror (or acceleration tracking mirror in two-mirror embodiments). For the next consecutive fields, the process is repeated using velocity error determined from positional information of the prior field (N−1) over time. The driving signal is determined as a function of this velocity error and sent to the motion tracking mirror for rotation during field N. FIG. 6 shows stage velocity error over time and also the approximate velocity error per field. The first arrow down from the stage velocity error indicates that determination of an average velocity error from the field, and the translation into a "same field" acceleration correction waveform. The feed forward mechanism is indicated by the second arrow down, translating this waveform to drive the mirror for the next field n based on the waveform derived from field n−1. In this manner, the stage velocity error is approximated for each field based on the prior field n−1.

In one embodiment, the field level feed forward mechanism proceeds according to the following steps:
a) Measure multiple positions of the substrate over field n−1.
b) Determine an average velocity for field n−1.
c) Calculate the velocity fluctuation for field n−1 and a correction term based on this velocity fluctuation.
d) Apply correction term to motion profile (e.g., an electric motor waveform) to send to driver or amplifier.

e) Send a driving signal to an electric motor operably linked to a motion tracking mirror or acceleration tracking mirror to generate movement of the tracking mirror during image capture of field n.

f) Repeat process for remaining fields in lane

In some embodiments, the total feedback loop in the servomechanism based on field level feed-forward velocity tracking is less than 100 ms, less than 90 ms, less than 80 ms, less than 70 ms, less than 60 ms, less than 50 ms, less than 40 ms, less than 30 ms, less than 20 ms, less than 10 ms, less than 5 ms, or less than 2 ms. In some embodiments, feed-forward velocity tracking is used to adjust the movement of an acceleration tracking mirror in the two mirror optical path alignment correction embodiment.

In some embodiments, in order to minimize error due to the linear ramp of an electric motor-controlled single mirror, the electric motor driving signal or waveform is adjusted to compensate for systematic errors in tracking. Minimization of error in generating a linear ramp (e.g., a forward scan or fly-back) of an electric motor can also be achieved by reducing the speed of motion of the mirror, such as by reducing the imaging frequency of the optical scanning system. In some embodiments, the frequency of the sawtooth waveform to control the electric motor in the single mirror embodiment is kept at or below 200 Hz. In some embodiments, the frequency of the sawtooth waveform to control the electric motor in the single mirror embodiment is from 50 Hz to 30 Hz. In some embodiments, the frequency of the sawtooth waveform to control the electric motor in the single mirror embodiment is from 45 Hz to 35 Hz. In some embodiments, the duty cycle of the sawtooth waveform to control the electric motor in the single mirror embodiment is 70% or less. In some embodiments, the duty cycle of the sawtooth waveform to control the electric motor in the single mirror embodiment is from 60% to 80%. In some embodiments, the frequency of image capture and the duty cycle in the single mirror embodiment are adjusted to have a total velocity tracking error of less than 2%. In some embodiments, the frequency of image capture and the duty cycle in the single mirror embodiment are adjusted to have a total pixel smear of less than 2 pixels or less than 1 pixel.

As discussed herein, according to some embodiments, the controller module refers to a collection of components including i) sensors to determine states of parts of the optical scanning system (e.g., a stage position sensor) for feedback control, ii) mechanisms that calculate or otherwise provides waveforms for effecting movement of components of the optical scanning device (e.g., a sawtooth wave to drive a velocity tracking mirror), or iii) mechanisms that send a driving signal to an actuator based on the waveform to effect movement of a component.

For example, as discussed above, the controller module can be used to create the correct waveforms to drive the movement of certain components, such as rotatable mirrors to adjust the optical path, and synchronize them to stage motion based on stage encoder or master clock values. The waveform for a velocity tracking mirror can be a sawtooth waveform with a ramp that tilts the velocity tracking mirror at the right speed to match of the velocity of the stage. The waveform sent to an acceleration tracking mirror or to a single rotatable mirror in the single mirror embodiment must include a term to correct for velocity fluctuations that occur in the moveable stage velocity. This waveform can be created by "mapping" out the stage velocity non-linearities using a reticle with calibration marks on it, or it can be created by taking the measured stage velocity from the previous field, creating a waveform that compensates for velocity non-linearities and using that waveform to correct for velocity fluctuations in the next field, i.e., the field level "feed-forward" approach. The waveform can also be created by providing information from a velocity fluctuation table to the controller module.

According to the techniques described herein, one or more computing devices and/or various logic thereof are configured and operative to control the coordinated motions of the scanning mirror or mirrors (e.g., the acceleration and velocity tracking mirrors) and the moveable stage. Thus, in some embodiments the moveable stage (and therefore the substrate mounted thereon) can be configured to move with constant velocity, in which case the back-scan motion of the tracking mirror will also be at a suitable constant velocity. In other embodiments, the moveable stage can be configured to move with non-constant velocity, in which case the back-scan motion of the tracking mirror will also be at a suitable non-constant constant velocity.

The controller module can also be used to synchronize components of the optical scanning device to enable capture of an image of a field of a substrate on a moving stage. In addition to linking motion of the rotatable mirrors to the velocity of a moveable stage, the controller module can also control other components of the device. In some embodiments, the controller module comprises a mechanism to control illumination of the field. For example, the controller module may send a signal to an illumination device, such as a laser, to time illumination with the image capture process. In some embodiments, illumination state is dependent upon the sawtooth waveform sent to a velocity tracking mirror. In some embodiments, the controller module sends a signal to control movement of the moveable stage at a selected velocity or along a selected path, such as a serpentine path to image several fields on a substrate.

Figure 7A:
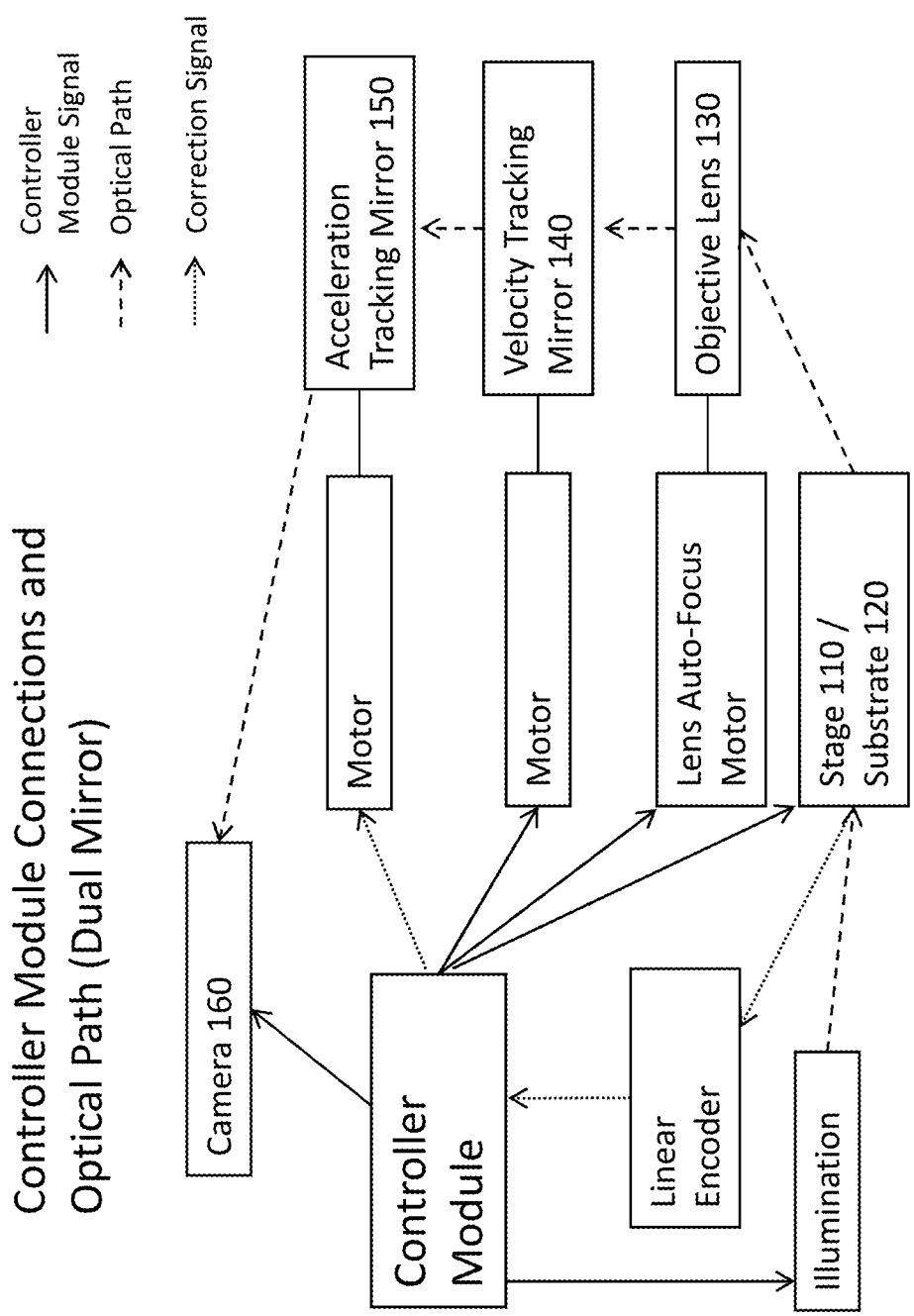
FIGS. 7A and 7B are diagrams of components of a controller module and its connections to certain components of the device, including the adjustable tracking mirror(s) and substrate or moveable stage position sensing devices. Connections are indicated by arrows. A solid arrow indicates a signal sent from the controller module to the respective component. Dotted arrow indicates the path for measurement of velocity fluctuations of the stage or substrate and translation into a driving signal that controls the motor operably connected to an acceleration or motion tracking mirror. Dashed arrows indicate the movement of light from along an optical path among components of the optical scanning system.
Figure 7B:
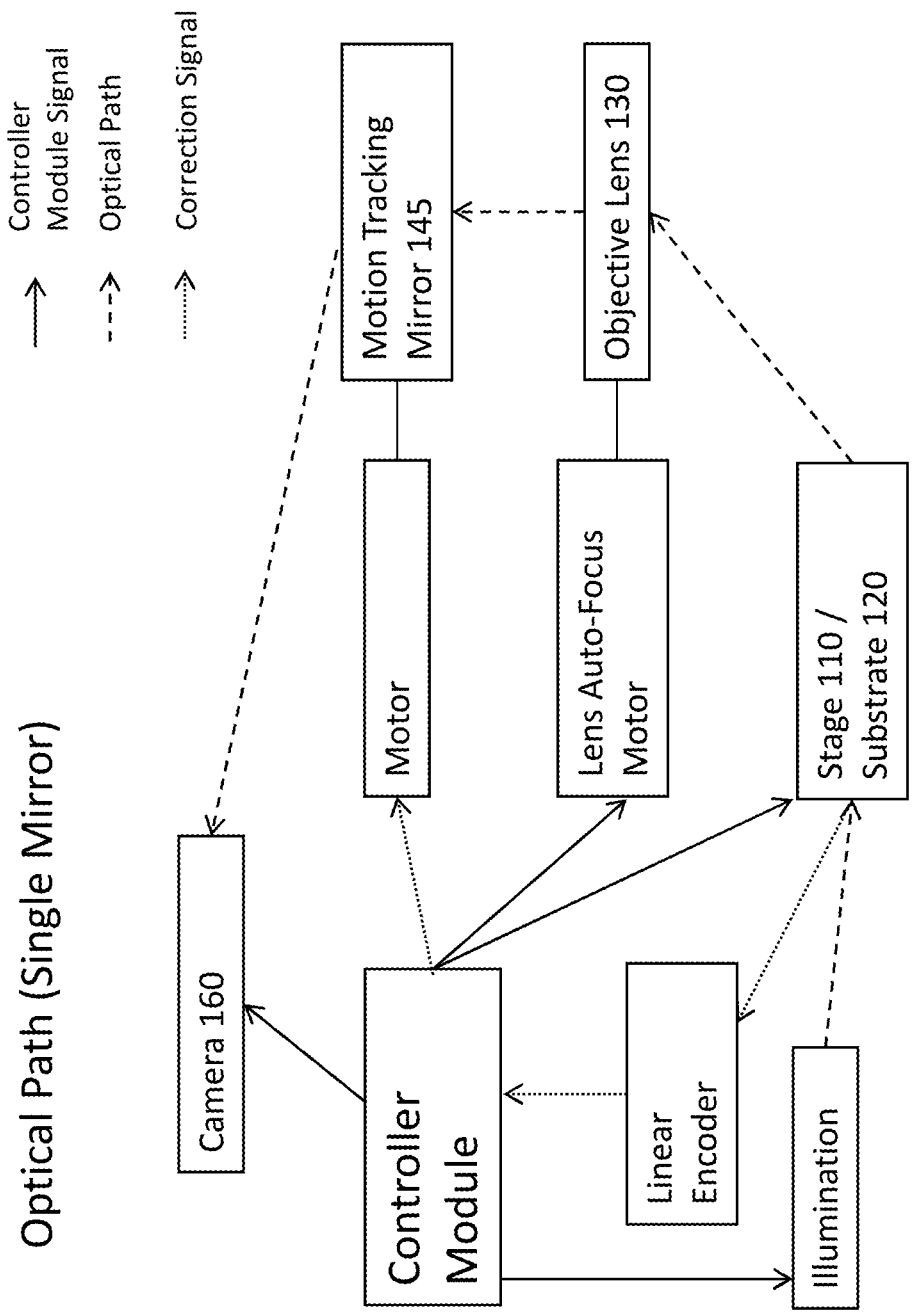

The connection of the controller module to certain components of an optical scanning system, according to a dual-mirror embodiment, is shown in FIG. 7A. As illustrated in this embodiment, the controller module is operably connected to an illumination component to control illumination of a substrate, such as by timing illumination with image capture timing. The controller module is operably connected to a camera to control image capture by the camera to coordinate with the motion of the rotating mirrors, e.g., such that an image is acquired during tracking of each field, and no image is acquired during the fly-back period of a tracking mirror. As described in more detail herein, the controller module can comprise a memory, a processor, and a driver. The memory can hold a predetermined velocity or velocity fluctuation information to be used by the processor to generate a waveform. The memory can also hold a predetermined waveform. The waveform can be sent to the driver to generate a driving signal. In some embodiments, the controller module is operably connected to an encoder (e.g., a linear encoder) to receive positional information about the moving stage over time. The controller module can then generate a drive signal as a function of velocity fluctuation from the information from the linear encoder, which can then be sent to the driver to send a driving signal to an acceleration tracking mirror (or substrate tracking mirror in the one-mirror embodiment (FIG. 7B)). The path from data collection from the stage to movement of a tracking mirror is indicated by the dotted arrows, which also include a driving signal sent from the controller module to a motor operably connected to an acceleration tracking mirror 150 or motion tracking mirror 145. FIGS. 7A and 7B also depicts the optical path of light from an illumination source to detection by the camera according to a dual-mirror embodiment. Solid lines (not arrows) in FIGS. 7A and 7B indicate an operable connection between a motor and a component of the device actuated by the motor.

In an example embodiment, the optical scanning system further comprises an illumination light source. In various embodiments, the illumination source can emit light of various wavelengths that are compatible with various fluorophores that can be used in biomolecular detection, for example, light of wavelength in a range from 400 nm to 800 nm. In some embodiments, the illumination source is mounted underneath the substrate, such that light collected by the objective lens is transmitted through the field to the objective lens. In other embodiments, the illumination source is mounted above the substrate, such that light collected by the objective lens is reflected by the field to the objective lens.

The optical scanning system can further comprise a dichroic mirror. In an example embodiment, the optical scanning system further comprises an illumination source and a dichroic mirror, where the dichroic mirror is configured and operative at least to: (a) reflect light from the illumination source to illuminate a field of the substrate or a portion thereof; and (b) pass through light that is emitted by the sample and passes through the objective lens.

In some embodiments, the optical scanning system further comprises a splitter. The splitter can be placed along the optical path after the acceleration and velocity tracking mirrors (or single tracking mirror) to split the optical signal comprising the field image to two or more cameras.

The optical scanning system can also comprise a tube lens component positioned in an optical path between the tracking mirror and the objective lens, so that the tracking mirror can be situated at the pupil of the objective lens. Relay lenses or tube lenses may also be used along the optical path at other locations to invert an image or to extend the optical path.

In some embodiments, the optical scanning system comprises a relay lens system used to create a region in the optical path which has all rays nominally parallel and also has a small beam diameter. In some embodiments, scanning optical elements are placed where the optical path has a small beam diameter to ensure that their placement: (i) minimizes power loss, (ii) minimizes image degradation and (iii) minimizes the size of the optical elements so that their mass can be as small as possible. This enables higher scanning frequencies and a lighter weight system.

The use of a relay lens system can facilitate fluorescence-based optical scanning systems that are used used for biomolecular detection on a substrate, as these systems typically employ very low light levels with dim fluorescence images. Thus, relay lenses are effective to increase the efficiency and sensitivity of the optical scanning system to keep image acquisition time to a minimum. Further, in some embodiments, illumination intensity must remain below the point where it can damage biomolecules on the substrate.

Figure 8A:
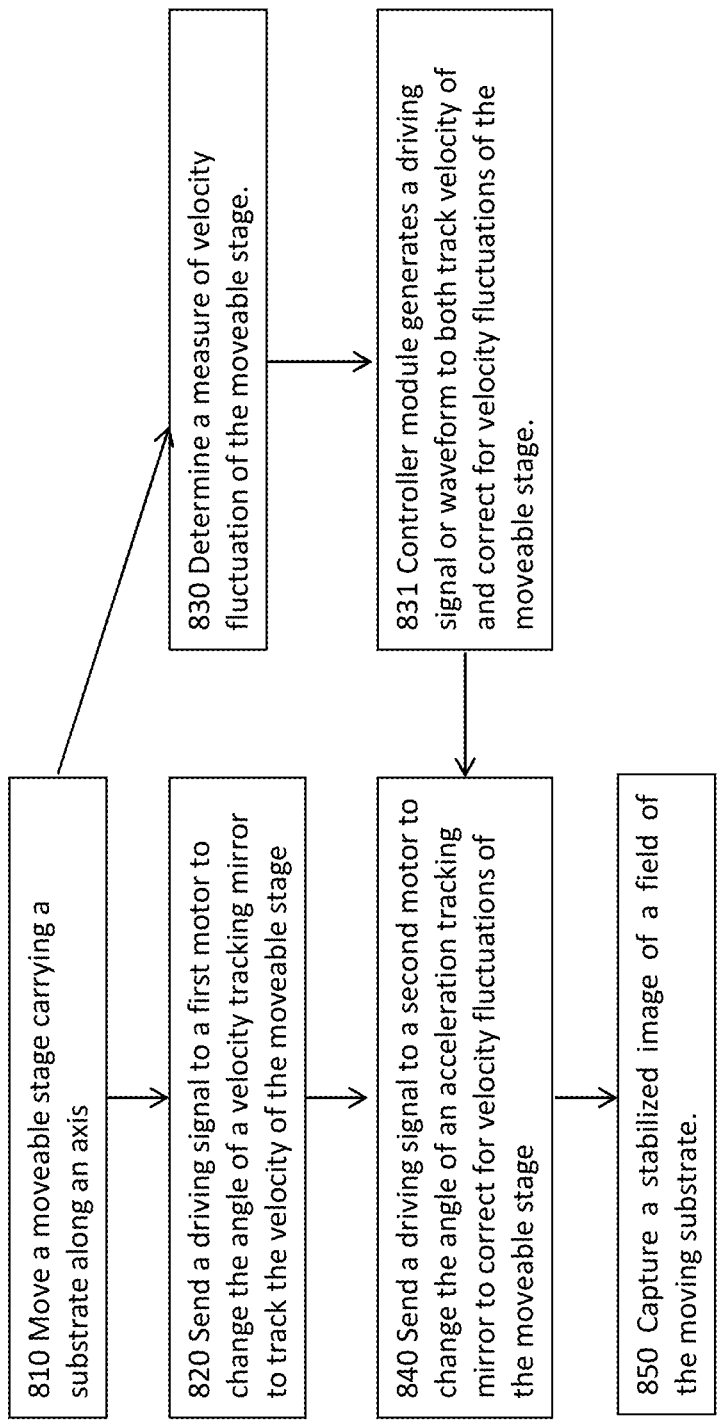
FIG. 8A provides a flowchart of a method of operating a dual tracking mirror embodiment of a device to capture a stabilized image of a field of a moving substrate.

FIG. 8A illustrates an example method for imaging a substrate according to a dual-mirror embodiment. The method in FIG. 8A is not limited to being performed by any particular type of machine or device, and therefore the method description hereinafter is to be regarded in an illustrative rather than a restrictive sense.

In step 810, a moveable stage moves a substrate under an objective lens in a plane that is normal to the optical axis of the objective lens. While the substrate is in motion, in step 820, a servo mechanism (e.g., an electric motor) changes the angle of a velocity tracking mirror to track the velocity of the moving stage during the capture of an image of a field of the substrate. In some aspects, a controller module that is part of or coupled to, the velocity tracking mirror executes logic that controls the servo mechanism operably connected to the velocity tracking mirror. In step 840 a servo mechanism changes the angle of an acceleration tracking mirror to track velocity fluctuations of the moving stage during the capture of an image of a field of the substrate. In some aspects, a controller module that is part of or coupled to, the acceleration tracking mirror executes logic that controls the servo mechanism in coordination with the moveable stage. In some embodiments, logic receives feedback control information that represents the movement (e.g., velocity fluctuations) of the moveable stage and uses this information to adjust the input signal to the servo mechanism, which in turn changes the angle of the acceleration tracking mirror, thereby synchronizing the combined motion of the velocity tracking mirror and acceleration tracking mirror with the movement of the moveable stage. In some aspects, this feedback information is received 831 from an linear controller that detects whether there are any nonlinearities in the motion of the moveable stage 830. The logic then uses this information to compute offset corrections and passes the offset corrections as an input signal to a servo mechanism that controls the angle of the acceleration tracking mirror in the optical path between the tracking mirror and the camera. In this manner, by making minor adjustments to the angle of the acceleration tracking mirror, the logic effectively removes from the image being acquired any errors that are caused by nonlinearities in the motion of the moveable stage.

In step 850, the camera records the still image of the substrate (or a portion thereof) while the substrate is being moved by the moveable stage.

Figure 8B:
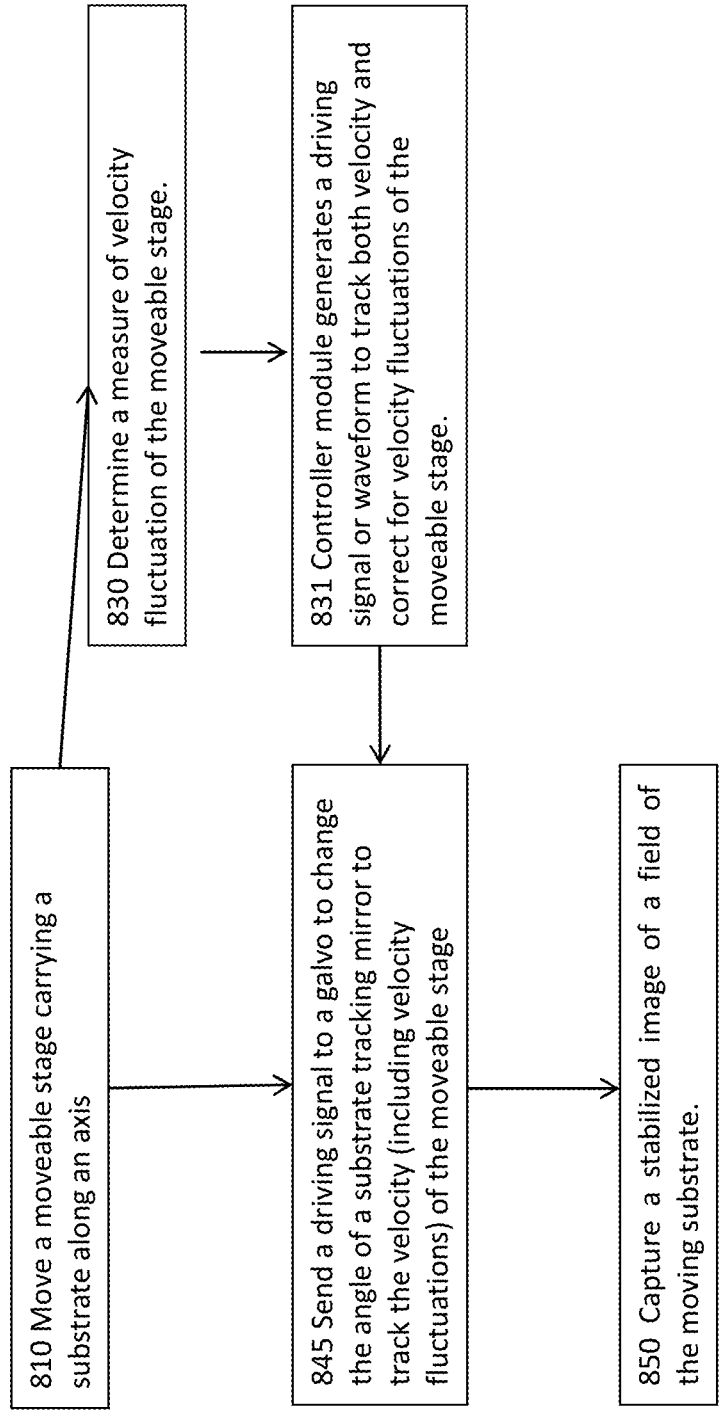
FIG. 8B provides a flowchart of a method of operating a single tracking mirror embodiment of a device to capture a stabilized image of a field of a moving substrate.

FIG. 8B illustrates an example method for imaging a substrate according to a single-mirror embodiment. The method in FIG. 8B is not limited to being performed by any particular type of machine or device, and therefore the method description hereinafter is to be regarded in an illustrative rather than a restrictive sense.

In step 810, a moveable stage moves a substrate under an objective lens in a plane that is normal to the optical axis of the objective lens, where the substrate comprises a multitude of distinct features that are the targets of the imaging.

While the substrate is in motion, in step 845 a servo mechanism changes the angle of a motion tracking mirror to track velocity fluctuations of the moving stage during the capture of an image of a field of the substrate. In some aspects, a controller module that is part of or coupled to, the motion tracking mirror executes logic that controls the servo mechanism in coordination with the moveable stage. In some embodiments, logic receives feedback control information that represents the movement (e.g., velocity fluctuations) of the moveable stage and uses this information to adjust the input signal to the servo mechanism, which in turn changes the angle of the motion tracking mirror to compensate for velocity fluctuations of the moveable stage. In some embodiments, the controller module incorporates the velocity fluctuation of the moveable stage into a sawtooth waveform for tracking a predetermined velocity, which is used as a driving signal to control movement of the motion tracking mirror. In some aspect, this feedback information is received 831 from an linear controller that detects whether there are any nonlinearities in the motion of the moveable stage 830. The logic then uses this information to compute offset corrections and passes the offset corrections as an input signal to a servo mechanism that controls the angle of the motion tracking mirror in the optical path. In this manner, by making minor adjustments to the angle of the motion tracking mirror, the logic effectively removes from the image being acquired any errors that are caused by nonlinearities in the motion of the moveable stage.

In step 850, the camera records the still image of the substrate (or a portion thereof) while the substrate is being moved by the moveable stage.

Optical scanning systems provided herein compensate for stage velocity (or any other imaging of moving components) non-linearities (e.g., local stage accelerations) that would normally result in a blurry image in a device that tracks only stage velocity, but does not have a mechanism to compensate for stage velocity fluctuations. In some embodiments, the optical scanning system is capable of generating stabilized images of a continuously moving substrate or other object at 30 frames per second. In some embodiments, the optical scanning system is capable of generating still images of a continuously moving substrate or other object at from 10 to 30 frames per second. In some embodiments, the optical scanning system is capable of generating still images of a continuously moving substrate or other object at 40 frames per second. In some embodiments, the optical scanning system is capable of generating still images of a continuously moving substrate or other object at more than 30 frames per second, 40 frames per second, 50 frames per second, 60 frames per second, 70 frames per second, 80 frames per second, 90 frames per second, 100 frames per second, 120 frames per second, 150 frames per second or 200 frames per second.

In some embodiments, the stage velocity fluctuation of the optical scanning system is greater than +/−0.5%. In some embodiments, the stage velocity fluctuation of the optical scanning system is greater than +/−0.1%. In some embodiments, the stage velocity fluctuation of the optical scanning system is greater than +/−0.1%, and is reduced to less than +/−0.1% as observed by the camera.

In some embodiments, the stage velocity fluctuation of the optical scanning system is greater than +/−1%. In some embodiments, the stage velocity fluctuation of the optical scanning system is greater than +/−1%, and is reduced to less than +/−1% as observed by the camera.

In some embodiments, the optical scanning system described herein provides an increased sharpness of an image over a system that does not compensate for velocity fluctuations in a continuously moving stage.

In some embodiments, the total distance a substrate moves during the imaging of a field deviates by more than +/−1 pixel (as measured by the image of the substrate projected onto the sensor) from a predetermined movement based on an anticipated velocity during a capture of a field image, while the optical scanning system generates an image with a pixel blur of less than 1. In some embodiments, a pixel is correlated to an area of the field of ~150 nm×150 nm. In some embodiments, a pixel is correlated to an area of the field of ~162.5 nm×162.5 nm. In some embodiments, a pixel is correlated to an area of the field that is greater than the size of a single fluorophore.

Pixel smear is one measure of image sharpness and refers to an image artifact that results from the movement of a substrate in an optical field with respect to an image sensor. One way to measure pixel smear is by looking at the ratio of the major and minor axes of a single spot, also known as the eccentricity. In some embodiments, the eccentricity of an image generated by the optical scanning system is less than 3. In some embodiments, the eccentricity of the image is reliable single fluorophore detection.

Figure 9A:
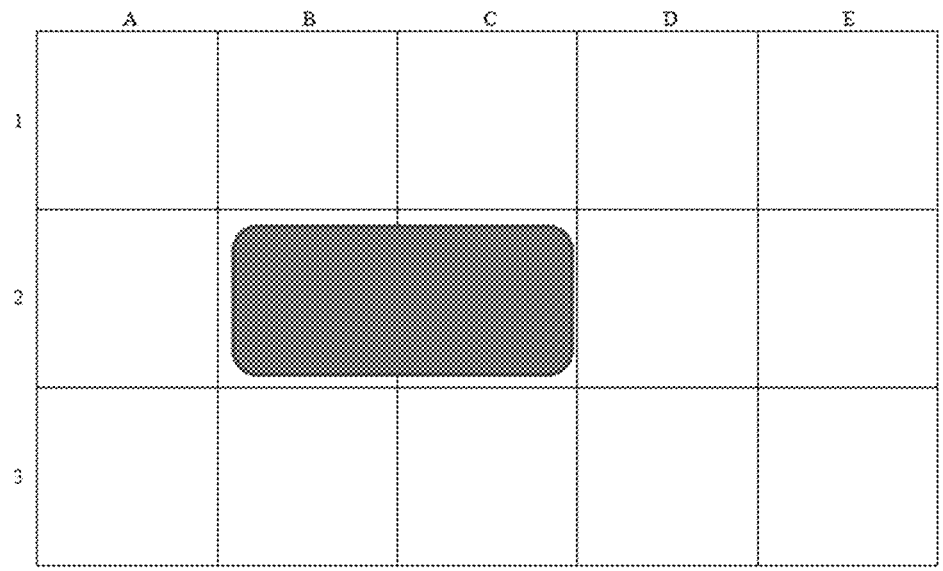
FIGS. 9A and 9B illustrate an example of a pixel smear of an image of +1 and +2 respectively. Each square represents a pixel.
Figure 9B:
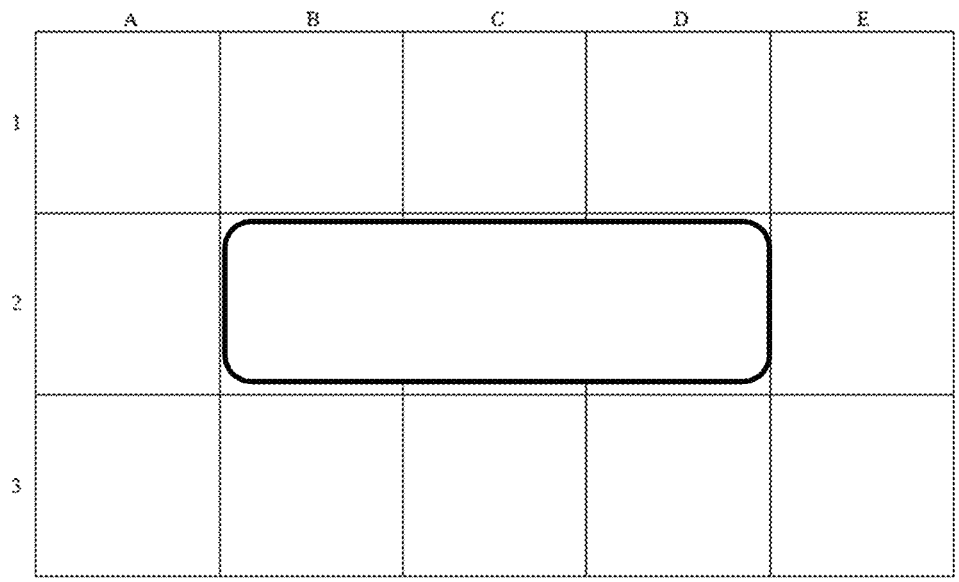

FIGS. 9A and 9B provides an example of pixel smear and eccentricity of a resulting image of a substrate from the optical scanning system provided herein. The blue spot represents a single illuminated fluorophore, and each square is a pixel of ~162 nm. Shown in FIG. 9A is an example of a pixel smear of +1 pixel, within a preferred range of +/−1 pixel, with an eccentricity of 2. Shown in FIG. 9B is an example of a pixel smear of +2 pixels, outside of the preferred range of +/−one pixel, with an eccentricity of 3.

Figure 10:
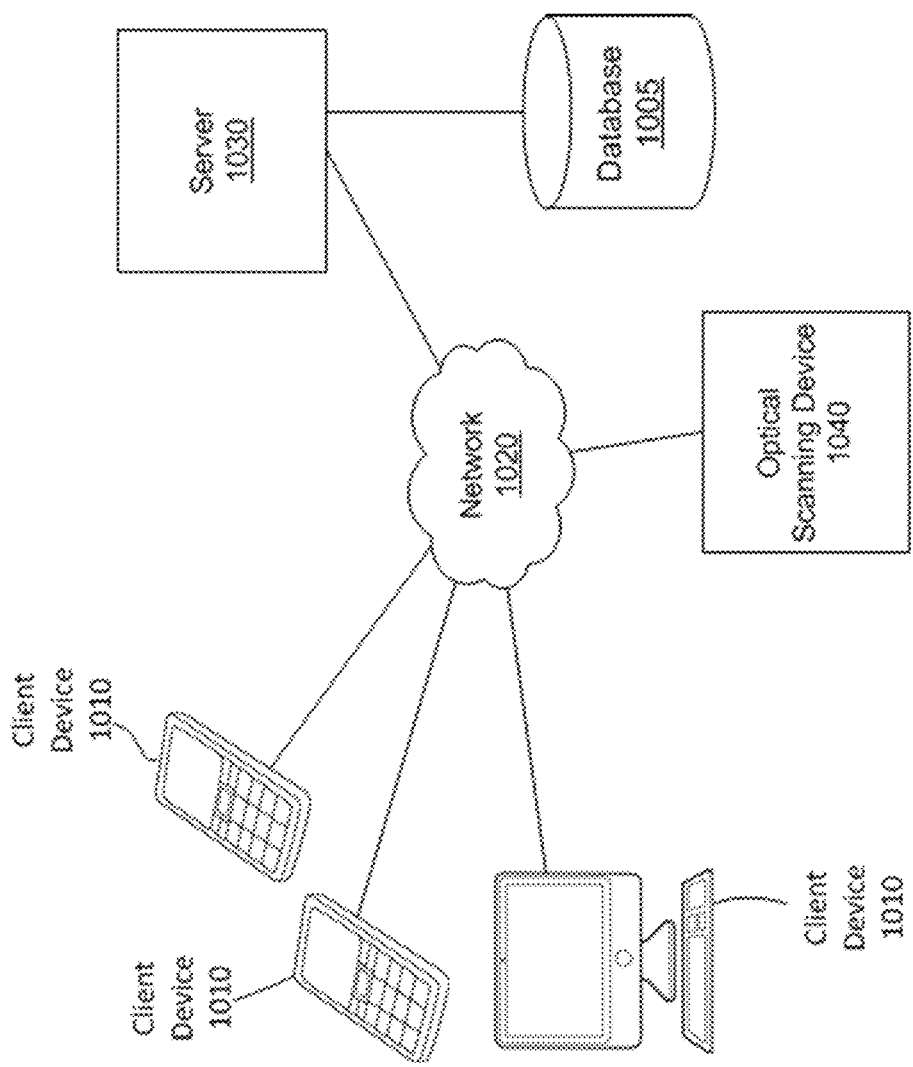
FIG. 10 illustrates an embodiment of the optical scanning system, including components for controlling and storing data from the system.

FIG. 10 illustrates a system environment for transferring information to or from the optical scanning device. The system environment can include one or more client devices 1010, one or more servers 1030, a database 1005 accessible to the server 1030, where all of these parties are connected through a network 1020. In other embodiments, different and/or additional entities can be included in the system environment.

The system environment allows the results from the optical scanning device 1040 to be shared via network 1020 with one or more other users at their client devices 1010. Results can also be uploaded to the web.

The network 1020 facilitates communications between the components of the system environment. The network 1020 may be any wired or wireless local area network (LAN) and/or wide area network (WAN), such as an intranet, an extranet, or the Internet. In various embodiments, the network 1020 uses standard communication technologies and/or protocols. Examples of technologies used by the network 1020 include Ethernet, 802.11, 3G, 4G, 802.16, or any other suitable communication technology. The network 1020 may use wireless, wired, or a combination of wireless and wired communication technologies. Examples of networking protocols used for communicating via the network 1020 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 1020 may be represented using any suitable format, such as hypertext markup language (HTML) or extensible markup language (XML). In some embodiments, all or some of the communication links of the network 1020 may be encrypted using any suitable technique or techniques.

The client device(s) 1010 are computing devices capable of receiving user input as well as transmitting and/or receiving data via the network 1020. In one embodiment, a client device 1010 is a conventional computer system, such as a desktop or laptop computer. Alternatively, a client device 1010 may be a device having computer functionality, such as a personal digital assistant (PDA), a mobile telephone, a smartphone or another suitable device. A client device 1010 is configured to communicate via the network 1020.

In some embodiments, the system environment may include one or more servers, for example where the diagnostic system is includes a service that is managed by an entity that communicates via the network 1020 with the optical scanning device 1040 and/or any of the client devices 1010. The server 1030 can store data in database 1005 and can access stored data in database 1005. The server 1030 may also store data in the cloud. In some embodiments, the server 1030 may occasionally push updates to the optical scanning device 1040, or may receive result data from the optical scanning device 1040 and perform certain analyses on that result data and provide the analyzed data back to the optical scanning device 1040 or to a client device 1010.

In some embodiments, the optical scanning device 1040 functionality can be included in a client device 1010, such as a mobile phone, and can be operated via a mobile application installed on the phone. The mobile application stored on the phone can process the results read from the optical scanning device and share the results with other devices 810 on the network 820.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

The invention claimed is:

1. An optical scanning system for imaging a moving substrate, comprising:
   a. a stage, said stage capable of moving along an axis, said stage configured to hold a substrate comprising a plurality of fields;
   b. an objective lens;
   c. a camera capable of acquiring an image of one of said plurality of fields through the objective lens, said image acquired via an optical path defined from one of said plurality of fields through said objective lens to said camera during acquisition of said image;
   d. a velocity tracking mirror mounted along said optical path;
   e. a first electrical motor operably coupled to said velocity tracking mirror to adjust the angle of the tracking mirror along said axis of stage movement in said optical path;
   f. a controller module operably coupled to said first electrical motor to send a first driving signal to said first electrical motor, wherein said first driving signal is a function of a velocity measurement of the stage movement along said axis;
   g. an acceleration tracking mirror mounted along said optical path, wherein a movement of said velocity tracking mirror and said acceleration tracking mirror reduce a tracking error of said plurality of fields by said camera as compared to without a movement of said acceleration tracking mirror; and
   h. a second electrical motor operably coupled to said acceleration tracking mirror to adjust the angle of the acceleration tracking mirror along said axis of stage movement in said optical path, wherein said controller module is operably coupled to said second electrical motor to send a second driving signal to said second electrical motor, wherein said second driving signal is a function of the change of the stage velocity along said axis.

2. The system of claim 1, wherein the tracking error is reduced to less than 0.1%.

3. The system of claim 1, wherein the tracking error is reduced to less than 1 pixel.

4. A method of imaging a plurality of fields on a moving substrate, comprising
   a. providing an optical scanning system comprising:
      i. a moveable stage holding a substrate comprising a plurality of fields,
      ii. a camera,
      iii. an objective lens,
      iv. a velocity tracking mirror, and
      v. an acceleration tracking mirror, wherein a movement of said velocity tracking mirror and said acceleration tracking mirror reduce a tracking error of said plurality of fields by said camera as compared to without a movement of said acceleration tracking mirror;
   b. moving said moveable stage along an axis, thereby moving said substrate comprising a plurality of fields along said axis; and
   c. concurrent with said movement, capturing an image of one of said plurality of fields passing through said objective lens using said camera, wherein said image of said field is stabilized during said image capture by:
      i. rotating said velocity tracking mirror as a function of a velocity of the moveable stage along said axis, and
      ii. rotating said acceleration tracking mirror as a function of a change in the velocity of the moveable stage along said axis.

5. The method of claim 4, wherein the tracking error is reduced to less than 0.1%.

6. The method of claim 4, wherein the tracking error is reduced to less than 1 pixel.

7. A method of imaging a plurality of fields on a moving substrate, comprising
   a. providing an optical scanning system comprising:
      i. a moveable stage holding a substrate comprising a plurality of fields,
      ii. a camera,
      iii. an objective lens,
      iv. a velocity tracking mirror, and
      v. an acceleration tracking mirror;
   b. moving said moveable stage along an axis, thereby moving said substrate comprising a plurality of fields along said axis;
   c. concurrent with said movement, capturing an image of one of said plurality of fields passing through said objective lens using said camera, wherein said image of said field is stabilized during said image capture by:
  i. rotating said velocity tracking mirror as a function of a velocity of the moveable stage along said axis, and
  ii. rotating said acceleration tracking mirror as a function of a change in the velocity of the moveable stage along said axis; and
d. a second velocity tracking mirror and a second acceleration tracking mirror, further comprising, concurrent with said movement of said moveable stage and said image capture of one of said plurality of fields:
  i. rotating said second velocity tracking mirror as a function of a velocity of the moveable stage along a second axis, and
  ii. rotating said second acceleration tracking mirror as a function of a velocity fluctuation of the moveable stage along said second axis thereby stabilizing imaging of said field for at least two axes simultaneously.

8. A method of imaging a plurality of fields on a moving substrate, comprising
a. providing an optical scanning system comprising:
  i. a moveable stage holding a substrate comprising a plurality of fields,
  ii. an objective lens,
  iii. a camera,
  iv. a motion tracking mirror, and
  v. an electric motor operatively coupled to said motion tracking mirror to effect movement of said motion tracking mirror to track said movement of said moveable stage along said axis during an image capture, and to return said motion tracking mirror to an initial position after said image capture;
b. moving said moveable stage along an axis, thereby moving said substrate comprising a plurality of fields along said axis; and
c. generating an image for each of M fields of said substrate, comprising performing at least M image capture cycles during movement of said moveable stage along said axis, each cycle comprising:
  i. providing a cycle M driving signal to an electric motor to control movement of said tracking mirror to track the velocity of said moveable stage along said axis;
  ii. capturing an image of said field while said tracking mirror is tracking said moving stage; and
  iii. determining an average velocity of said field, wherein said average velocity is used to generate a cycle M+1 driving signal to control movement of said electric motor during cycle M+1.

* * * * *